United States Patent
Cheong et al.

(10) Patent No.: US 7,919,008 B2
(45) Date of Patent: *Apr. 5, 2011

(54) LIQUID CRYSTAL COMPOSITION COMPRISING NOVEL SILICON CONTAINING COMPOUNDS AND LIQUID CRYSTAL DISPLAY DEVICE USING THE SAME

(75) Inventors: Jae Ho Cheong, Daejeon (KR); Min Jin Ko, Daejeon (KR); Dae Ho Kang, Daejeon (KR); Ki Youl Lee, Daejeon (KR); Youn Bong Kim, Seoul (KR)

(73) Assignee: LG Chem, Ltd., Seoul (KR)

( * ) Notice: Subject to any disclaimer, the term of this patent is extended or adjusted under 35 U.S.C. 154(b) by 128 days.

This patent is subject to a terminal disclaimer.

(21) Appl. No.: 11/330,170

(22) Filed: Jan. 12, 2006

(65) Prior Publication Data

US 2006/0151743 A1 Jul. 13, 2006

(30) Foreign Application Priority Data

Jan. 13, 2005 (KR) .................. 10-2005-0003157

(51) Int. Cl.
C09K 19/00 (2006.01)
C09K 19/06 (2006.01)
C09K 19/52 (2006.01)

(52) U.S. Cl. ............. 252/299.01; 252/299.2; 252/299.3; 252/299.4; 252/299.5; 252/299.6; 252/299.7; 430/20; 428/1.1; 428/1.2; 428/1.21; 345/175

(58) Field of Classification Search .... 252/299.1–299.7, 252/299.01; 430/20, 270.1; 428/1.1, 1.2; 345/176

See application file for complete search history.

(56) References Cited

U.S. PATENT DOCUMENTS

| | | | |
|---|---|---|---|
| 4,730,904 A | 3/1988 | Pauluth et al. | |
| 4,864,027 A * | 9/1989 | Shubert et al. | 546/14 |
| 5,399,290 A | 3/1995 | Häberle et al. | |
| 5,498,368 A | 3/1996 | Coles | |
| 5,595,684 A | 1/1997 | Namekawa et al. | |
| 5,641,431 A | 6/1997 | Kinsho et al. | |
| 5,659,059 A | 8/1997 | Ogihara et al. | |
| 6,703,082 B1 * | 3/2004 | Wand et al. | 428/1.1 |
| 6,703,083 B2 | 3/2004 | Kato et al. | |
| 2001/0038091 A1 | 11/2001 | Yanai et al. | |
| 2002/0047103 A1 | 4/2002 | Sagou et al. | |
| 2003/0168632 A1 | 9/2003 | Kato et al. | |
| 2006/0151744 A1 * | 7/2006 | Cheong et al. | 252/299.62 |

FOREIGN PATENT DOCUMENTS

| | | |
|---|---|---|
| DE | 102 22 509 | 3/2003 |
| EP | 1 160 250 | 12/2001 |
| JP | 04-360890 | 12/1992 |
| JP | 7330753 | 12/1995 |
| JP | 08-239388 | 9/1996 |
| JP | 10-114894 | 5/1998 |
| JP | 11-029580 | 2/1999 |
| JP | 11-061133 | 3/1999 |
| JP | 2001-031685 | 2/2001 |
| JP | 2001335586 | 12/2001 |
| JP | 2002-255974 | 9/2002 |
| KR | 10-2003-0074467 A | 3/2003 |
| KR | 10-2006-0082821 | 7/2006 |
| WO | WO 03/040812 | 5/2003 |

* cited by examiner

Primary Examiner — Geraldina Visconti

(74) Attorney, Agent, or Firm — McKenna Long & Aldridge LLP

(57) ABSTRACT

Disclosed are a silicon-containing compound, a liquid crystal composition comprising the same compound, and a liquid crystal display device comprising a liquid crystal layer prepared from the liquid crystal composition. The silicon-containing compound, which forms the liquid crystal composition, has low viscosity and high negative (−) dielectric anisotropy. Therefore, it is possible to provide a liquid crystal display device, which has a fast response time and can be driven at a low voltage.

18 Claims, No Drawings

LIQUID CRYSTAL COMPOSITION COMPRISING NOVEL SILICON CONTAINING COMPOUNDS AND LIQUID CRYSTAL DISPLAY DEVICE USING THE SAME

This application claims the benefit of the filing date of Korean Patent Application No. 10-2005-0003157, filed on 13.01.2005, in the Korean Intellectual Property Office, the disclosure of which is incorporated herein in its entirely by reference.

TECHNICAL FIELD

The present invention relates to a novel silicon-containing compound and a liquid crystal composition comprising the same. More particularly, the present invention relates to a novel nematic liquid crystal compound, which has low viscosity and high negative dielectric anisotropy, a liquid crystal composition comprising the same compound, and a liquid crystal display device using the same composition.

BACKGROUND ART

In general, liquid crystal compounds having optical anisotropy ($\Delta n$) and dielectric anisotropy ($\Delta \epsilon$) are widely used in display devices such as clocks, notebook PCs, mobile phones, televisions and monitors. Such liquid crystal compounds are increasingly in demand. Liquid crystal compounds used in such display devices include a nematic liquid crystal phase, a smectic liquid crystal phase and a cholesteric liquid crystal phase. Among those phases, nematic phases are the most widely used. In practice, various liquid crystal compounds are used in the form of a composition. Liquid crystal compositions should be stable against water, light, heat, air, electric fields or the like, and have to ensure the chemical stability among the compounds forming the composition under the conditions of particular use. In order to use a liquid crystal compound in a display device, the liquid crystal compound should be in harmony of physical properties, including a wide range of liquid crystal phase temperatures, optical anisotropy value ($\Delta n$) and dielectric anisotropy value ($\Delta \epsilon$), viscosity and conductivity. Properties of a liquid crystal compound required for a display device depend on the specific type of the display device. Therefore, there is an imminent need for a novel liquid crystal device that satisfies the above properties at the same time. Recently, there has been a need for a liquid crystal display device having a fast response time in order to treat a great amount of information promptly.

DISCLOSURE OF THE INVENTION

Therefore, the present invention has been made in view of the above-mentioned problems. It is an object of the present invention to provide a novel liquid crystal compound, which has low viscosity as well as high negative dielectric anisotropy so as to permit optimization of display. It is another object of the present invention to provide a liquid crystal composition comprising the above compound. It is still another object of the present invention to provide a liquid crystal display device manufactured by using the above composition.

The present invention provides a novel silicon-containing compound represented by the following formula 1, a liquid crystal composition comprising the above compound, and a liquid crystal display device comprising a liquid crystal layer prepared from the above liquid crystal composition:

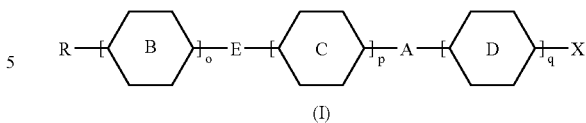

[Formula 1]

(I)

wherein A is selected from the group consisting of $SiMe_2O_{k1}(CQ_2)_{n1}$, $SiEt_2O_{k1}(CQ_2)_{n1}$, $SiF_2O_{k1}(CQ_2)_{n1}$, $SiCl_2O_{k1}(CQ_2)_{n1}$, $SiMe_2(CQ_2)_{n1}O_{k1}$, $SiEt_2(CQ_2)_{n1}O_{k1}$, $SiF_2(CQ_2)_{n1}O_{k1}$, $SiCl_2(CQ_2)_{n1}O_{k1}$, $O_{k1}SiMe_2(CQ_2)_{n1}$, $O_{k1}SiEt_2(CQ_2)_{n1}$, $O_{k1}SiF_2(CQ_2)_{n1}O_{k1}SiCl_2(CQ_2)_{n1}$, $(CQ_2)_{n1}O_{k1}SiMe_2$, $(CQ_2)_{n1}O_{k1}SiEt_2$, $(CQ_2)_{n1}O_{k1}SiF_2$, $(CQ_2)_{n1}O_{k1}SiCl_2$, $O_{k1}(CQ_2)_{n1}SiMe_2$, $O_{k1}(CQ_2)_{n1}SiEt_2$, $O_{k1}(CQ_2)_{n1}SiF_2$, $O_{k1}(CQ_2)_{n1}SiCl_2$, $(CQ_2)_{n1}SiMe_2O_{k1}$, $(CQ_2)_{n1}SiEt_2O_{k1}$, $(CQ_2)_{n1}SiF_2O_{k1}$, $(CQ_2)_{n1}SiCl_2O_{k1}$, $(CH_2)_{n1}$, $CH=CH$, $C\equiv C$, $O$, $S$, $COO$, $OCO$, $CF_2O$, $OCF_2$, $OCOO$, $CH_2O$, $CH_2CO$, $OCH_2$ and $COCH_2$, wherein $k_1$ is 0 or 1, Q is H or F, $n_1$ is an integer between 0 and 3;

ring B is selected from the group consisting of

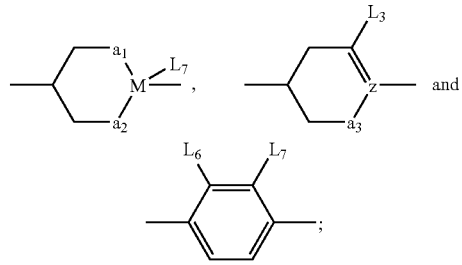

ring C is selected from the group consisting of

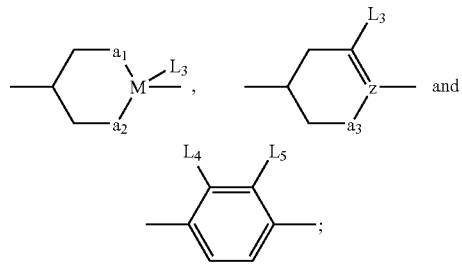

ring D is selected from the group consisting of

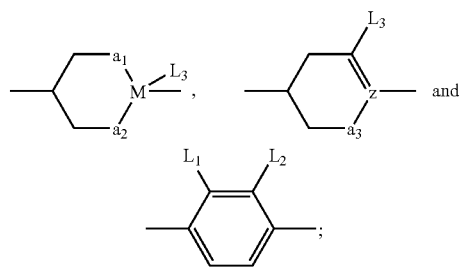

wherein the substituents, which are introduced into ring B, ring C or ring D and represented by $L_1$ to $L_7$, are independent from each other, even if they have the same designations;

M is selected from C, N and Si, with the proviso that if M is N, $L_3$ to $L_7$ is null;

Z is C;

each of $a_1$, $a_2$ and $a_3$ is independently selected from C, NR and O;

E is selected from the group consisting of $SiMe_2O_{k2}(CQ_2)_{n2}$, $SiEt_2O_{k2}(CQ_2)_{n2}$, $SiF_2O_{k2}(CQ_2)_{n2}$, $SiCl_2O_{k2}(CQ_2)_{n2}$, $SiMe_2(CQ_2)_{n2}O_{k2}$, $SiEt_2(CQ_2)_{n2}O_{k2}$, $SiF_2(CQ_2)_{n2}O_{k2}$, $SiCl_2(CQ_2)_{n2}O_{k2}$, $O_{k2}SiMe_2(CQ_2)_{n2}$, $O_{k2}SiEt_2(CQ_2)_{n2}$, $O_{k2}SiF_2(CQ_2)_{n2}$, $O_{k2}SiCl_2(CQ_2)_{n2}$, $(CQ_2)_{n2}O_{k2}SiMe_2$, $(CQ_2)_{n2}O_{k2}SiEt_2$, $(CQ_2)_{n2}O_{k2}SiF_2$, $(CQ_2)_{n2}O_{k2}SiCl_2$, $O_{k2}(CQ_2)_{n2}SiMe_2$, $O_{k2}(CQ_2)_{n2}SiEt_2$, $O_{k2}(CQ_2)_{n2}SiF_2$, $O_{k2}(CQ_2)_{n2}SiCl_2$, $(CQ_2)_{n2}SiMe_2O_{k2}$, $(CQ_2)_{n2}SiEt_2O_{k2}$, $(CQ_2)_{n2}SiF_2O_{k2}$, $(CQ_2)_{n2}SiCl_2O_{k2}$, $(CH_2)_{n2}$, C≡C, O, S, COO, OCO, $CF_2O$, $OCF_2$, OCOO, $CH_2O$, $CH_2CO$, $OCH_2$ and $COCH_2$, wherein $k_2$ is 0 or 1, Q is H or F, and $n_2$ is an integer between 0 and 3;

R is selected from the group consisting of H, a $C_1\sim C_{15}$ alkyl group, a $C_2\sim C_{15}$ alkene group and an alkoxy group ($R_1O$), wherein the alkene group is $CH=CH_2$, $CH=CHCH_3$ (E,Z), $CH_2CH=CH_2$, $CH=CHCH_2CH_3$ (E,Z), $CH_2CH=CHCH_3$ (E,Z), $CH_2CH_2CH=CH_2$, $CH=CHCH_2CH_2CH_3$ (E,Z), $CH_2CH=CHCH_2CH_3$ (E,Z), $CH_2CH_2CH=CHCH_3$ (E, Z) or $CH_2CH_2CH_2CH=CH_2$;

$R_1$ is selected from the group consisting of H, a $C_1\sim C_{15}$ alkyl group and a $C_2\sim C_{15}$ alkene group, wherein the alkene group is $CH=CH_2$, $CH=CHCH_3$ (E,Z), $CH_2CH=CH_2$, $CH=CHCH_2CH_3$ (E,Z), $CH_2CH=CHCH_3$ (E,Z), $CH_2CH_2CH=CH_2$, $CH=CHCH_2CH_2CH_3$ (E,Z), $CH_2CH=CHCH_2CH_3$ (E, Z), $CH_2CH_2CH=CHCH_3$ (E, Z) or $CH_2CH_2CH_2CH=CH_2$;

X is selected from the group consisting of H, $SiR_2R_3R_4$, $CF_3$, $OCF_3$, CN, NCS, halogen atoms and R;

each of $R_2$, $R_3$ and $R_4$ is independently selected from R and halogen atoms;

each of $L_1$, $L_2$, $L_3$, $L_4$, $L_5$, $L_6$ and $L_7$ is independently selected from the group consisting of H, halogen atoms, CN, $CF_3$, $OCF_3$ and NCS;

each of o, p and q independently represents an integer between 0 and 2; and at least one of E, A and X contains silicon.

Hereinafter, the present invention will be explained in more detail.

The present invention provides a novel silicon-containing compound that may be applied in various display devices, a liquid crystal composition essentially comprising the silicon-containing compound, preferably a negative nematic liquid crystal composition, and a liquid crystal display device using the above liquid crystal composition. The silicon-containing compound is characterized by having low viscosity, and high negative (−) dielectric anisotropy.

High dielectric anisotropy is required for the operation of a liquid crystal under a low driving voltage. According to the present invention, the liquid crystal compound has dissymmetry of substituents based on the major axis of the molecule, thereby providing high negative dielectric anisotropy.

Low viscosity is required to obtain a fast response time of a liquid crystal. According to the compound of the present invention, it is possible to obtain low viscosity by introducing a silicon-containing substituent into at least one of the linking groups (A and E) and terminal group (X), or both of the linking groups and terminal group.

Further, according to the present invention, it is possible to improve dipole moment by introducing a halogen atom and/or alkyl group as a substituent for the hydrogen atom, which forms a primary bond with silicon when a silicon-containing substituent is introduced into at least one of the linking groups and/or terminal group. Such improved dipole moment results in improvement in the dielectric anisotropy, which is affected significantly by the polarizability and dipole moment.

Preferred embodiments of the silicon-containing compound represented by formula 1 according to the present invention, which comprise preferred examples of ring B and ring C, are represented by the following formulae 2~10. However, the scope of the present invention is not limited thereto.

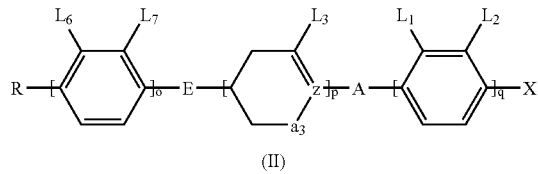

[Formula 2]

(II)

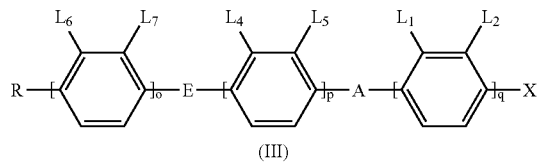

[Formula 3]

(III)

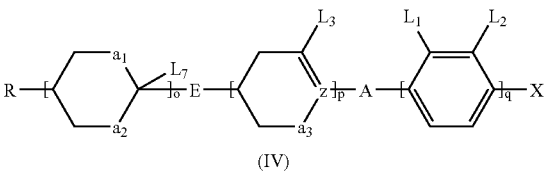

[Formula 4]

(IV)

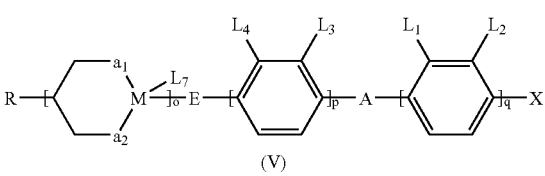

[Formula 5]

(V)

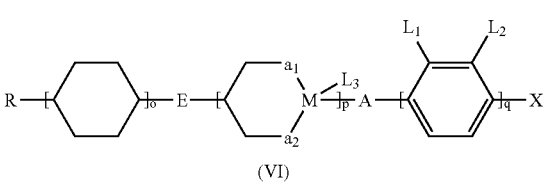

[Formula 6]

(VI)

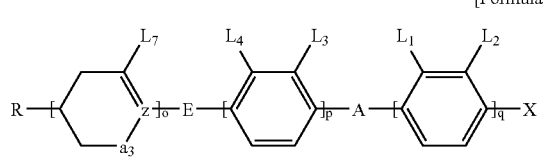

[Formula 7]

(VII)

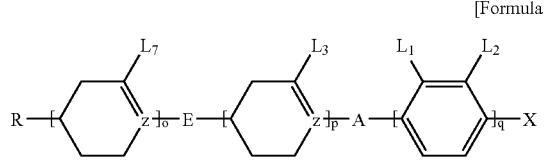

[Formula 8]

(VIII)

-continued

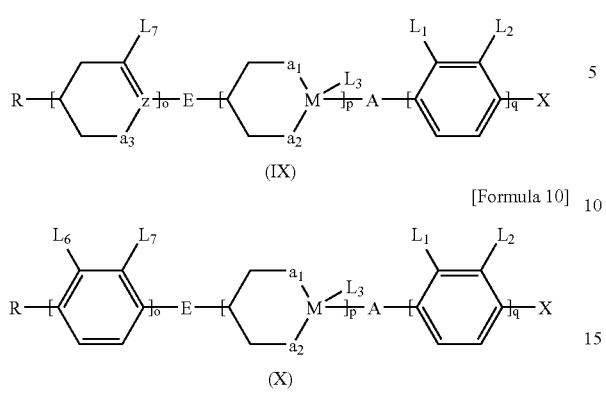

wherein Z is C;

M is C, N or Si, with the proviso that if M is N, $L_3$ or $L_7$ is null;

each of $a_1$, $a_2$ and $a_3$ is independently selected from C, NR and O;

each of $L_1$, $L_2$, $L_3$, $L_4$, $L_5$, $L_6$ and $L_7$ is independently selected from the group consisting of H, halogen atoms, CN, $CF_3$, $OCF_3$ and NCS; and A, E, R, X, o, p and q are the same as defined in formula 1.

Particular preferred examples of the compounds represented by formulae 2~10 include the following compounds. However, the scope of the present invention is not limited thereto.

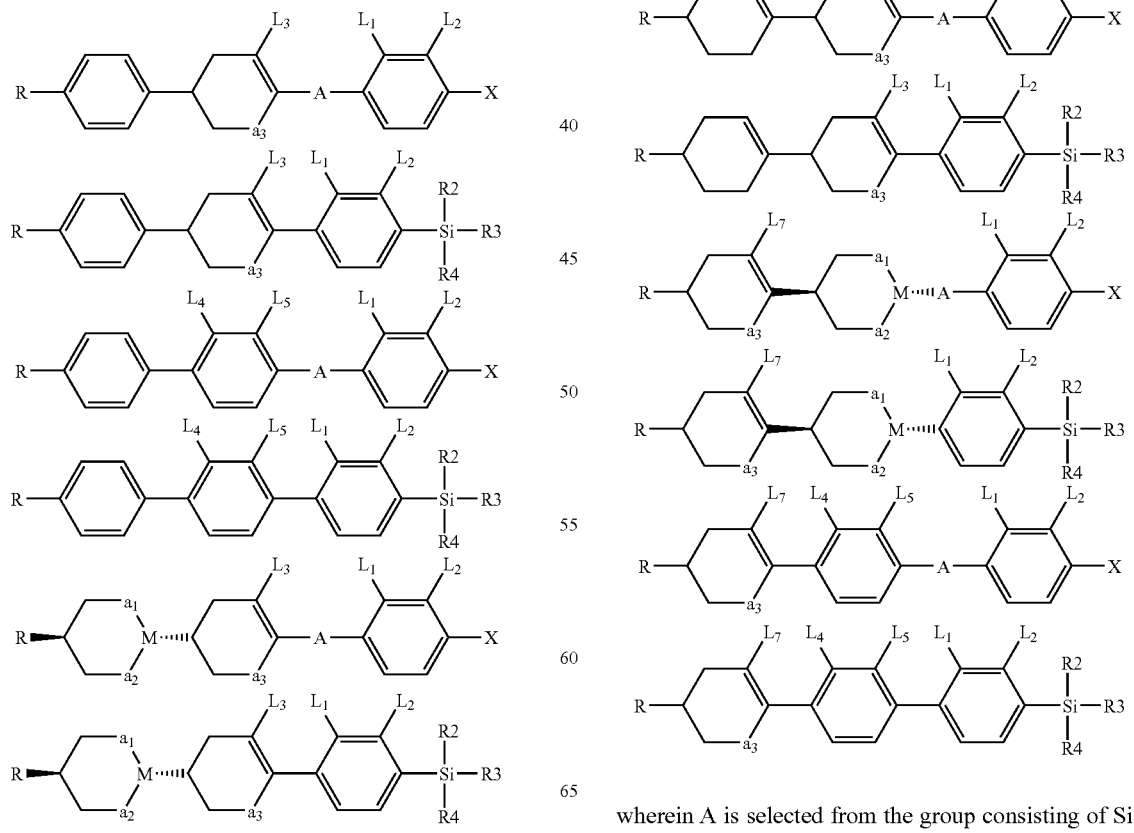

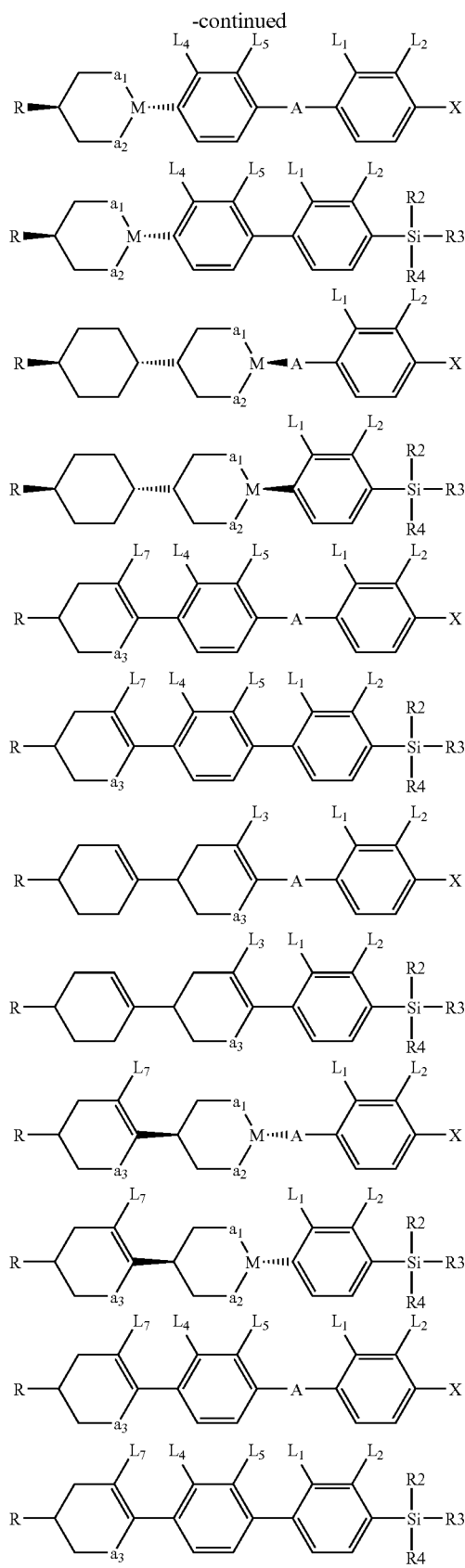

wherein A is selected from the group consisting of $SiO_{k1}$ $(CQ_2)_{n1}$, $Si(CQ_2)_{n1}O_{k1}$, $(CQ_2)_{n1}O_{k1}Si$, $(CQ_2)_{n1}SiO_{k1}$, $O_{k1}$ $(CQ_2)_{n1}Si$ and $O_{k1}Si(CQ_2)_{n1}$, and $k_1$, Q, $n_1$, R, $R_2$, $R_3$, $R_4$, M, $a_1$, $a_2$, $a_3$, $L_1$, $L_2$, $L_3$, $L_4$, $L_5$, $L_7$, and X are the same as defined in formula 1.

Stereoisomers of the silicon-containing compound represented by formula 1 are also included in the scope of the present invention. Herein, the silicon-containing compound having stereoisomers is present preferably in the trans-form with liquid crystal characteristics. Additionally, stereoisomers of the silicon-containing compound may be present in the ratio of trans-isomer:cis-isomer of 85~100:15~0, but are not limited thereto.

The novel silicon-containing compound represented by formula 1 is chemically and thermally stable, is stable to light, and can form a mesomorphic phase (meso-phase) at a desired temperature range so as to be used suitably for display applications.

The silicon-containing compound represented by formula 1 according to the present invention may be prepared by a method generally known to one skilled in the art. According to a preferred embodiment of the present invention, the silicon-containing compound represented by formula 1 may be prepared by way of the following Reaction Schemes 1~6.

[Reaction Scheme 1]

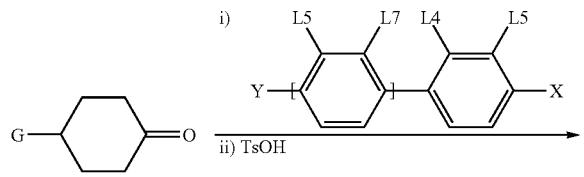

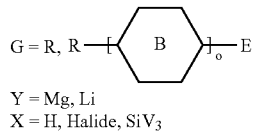

Y = Mg, Li
X = H, Halide, SiV₃

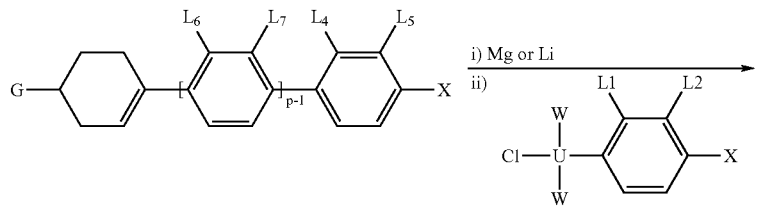

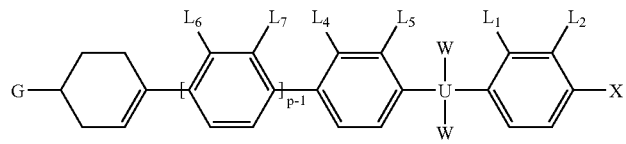

H₂ | Raney Ni

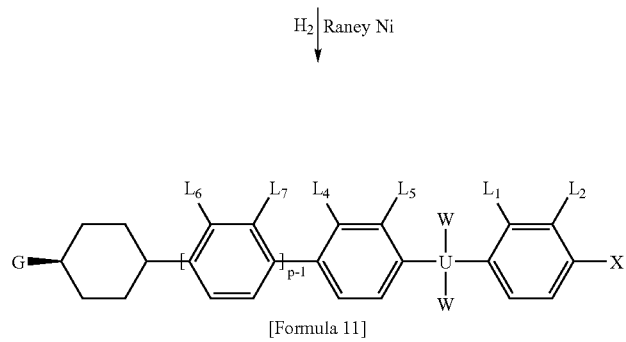

[Formula 11]

U = $SiO_{kl}(CQ_2)_{nl}Si(CQ_2)_{nl}O_{kii}(CQ_2)_{ni}O_{ki}Si_i(CQ_2)_{ni}SiO_{ki}$
W = Me, Et, F, Cl In one embodiment of the method represented by Reaction Scheme 1, 4-n-propylcyclohexanone is subjected to the Grignard reaction, followed by dehydration using TsOH. The resultant product is allowed to react with n-BuLi to form an anion, which in turn is allowed to react with a silyl chloride derivative. Next, hydrogenation is performed by using the Raney-Nickel catalyst in order to form a trans isomer, thereby providing a silyl liquid crystal compound represented by formula 11, in which ring B or ring C is 1,4-cyclohexyl. Otherwise, the trans isomer may be formed by way of hydrogenation using Pd/charcoal and recrystallization.

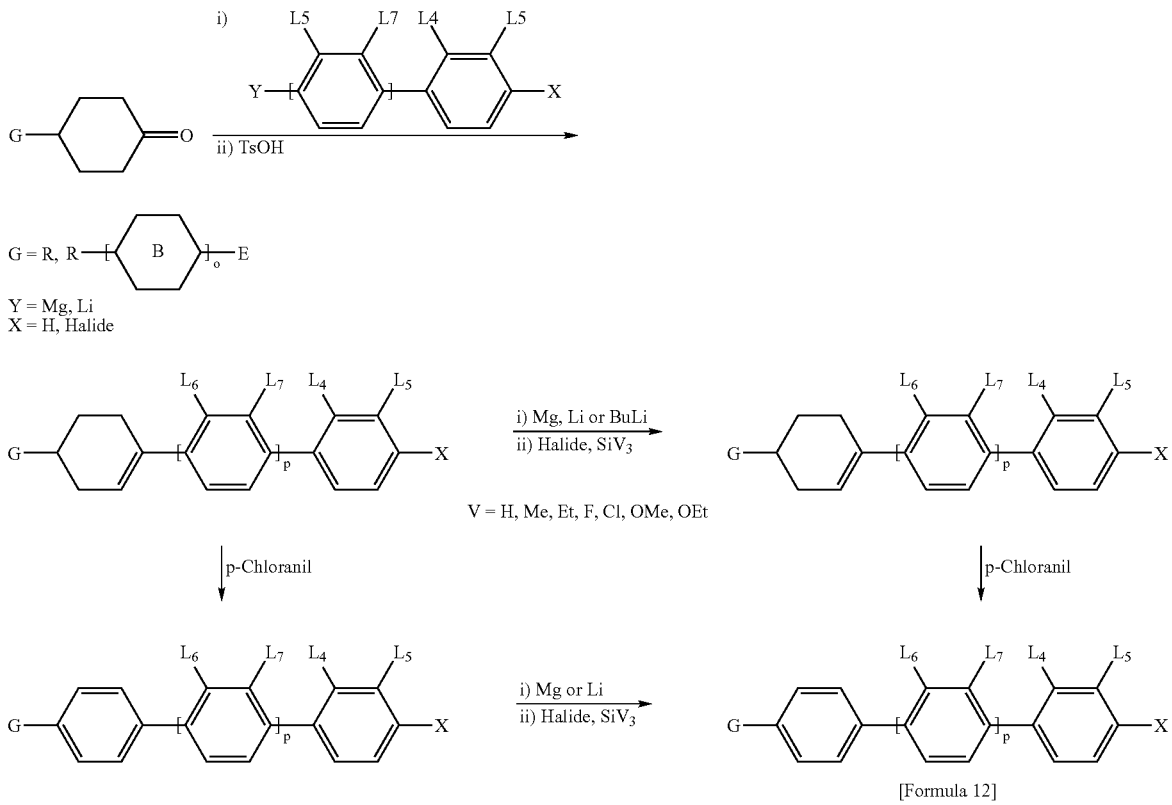

In one embodiment of the method represented by Reaction Scheme 2, 4-n-propylcyclohexanone is subjected to the Grignard reaction, followed by dehydration using TsOH. Then, the resultant product is converted into an anionic form by using n-BuLi, and then is allowed to react with the silyl chloride derivative. If the reaction with p-chloranil is used instead of hydrogenation, the silyl liquid crystal compound represented by formula 12, in which ring B or ring C is 1,4-phenyl, can be obtained.

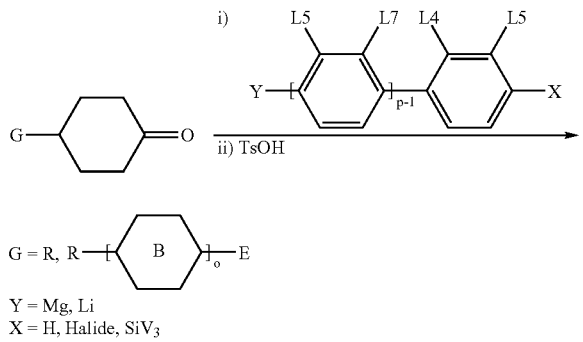

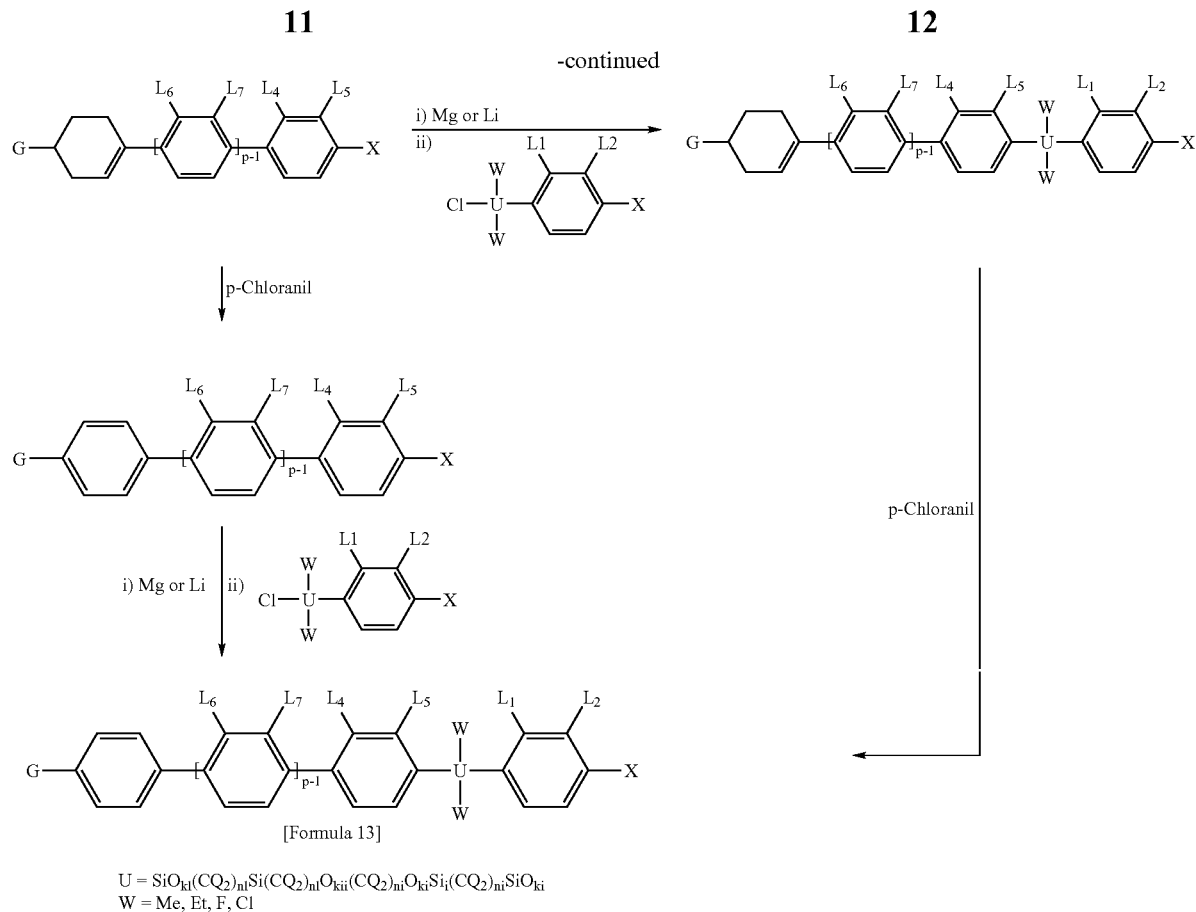

[Formula 13]

U = SiO$_{kl}$(CQ$_2$)$_{nl}$Si(CQ$_2$)$_{nl}$O$_{kii}$(CQ$_2$)$_{ni}$O$_{ki}$Si$_i$(CQ$_2$)$_{ni}$SiO$_{ki}$
W = Me, Et, F, Cl In one embodiment of the method represented by Reaction Scheme 3, 4-n-propylcyclohexanone is subjected to the Grignard reaction, followed by dehydration using TsOH. Next, the resultant product is converted into its anionic form by using n-BuLi, and then is allowed to react with the silyl chloride derivative. If the reaction with p-chloranil is used instead of hydrogenation, the silyl liquid crystal compound represented by formula 13, in which ring B or ring C is 1,4-phenyl, can be obtained.

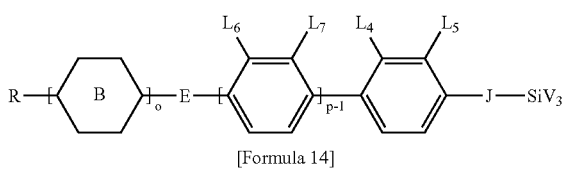

[Formula 14]

V = H, Me, Et, F, Cl, OMe, OEt

In one embodiment of the method represented by Reaction Scheme 4, Pd-coupling reaction is performed by using a boronic acid derivative to provide a biphenyl or triphenyl derivative, which, in turn, is converted into an anion by using n-BuLi. Then, the resultant product is allowed to react with the silyl chloride to provide the silyl liquid crystal compound represented by formula 14.

[Reaction Scheme 4]

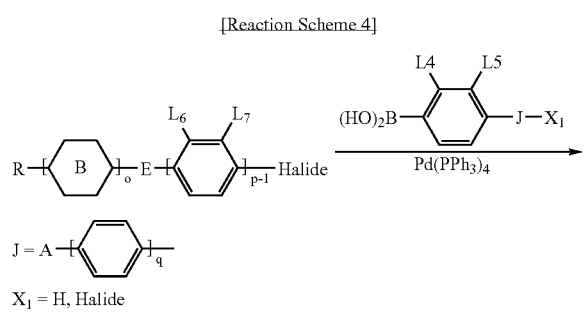

X$_1$ = H, Halide

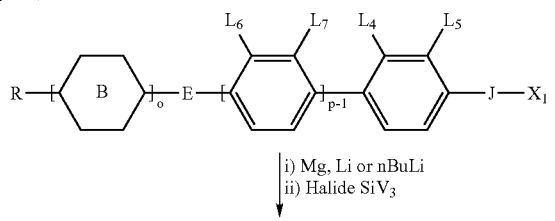

[Reaction Scheme 5]

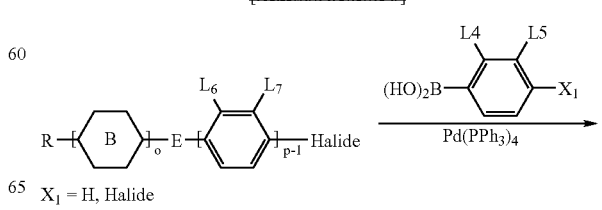

X$_1$ = H, Halide

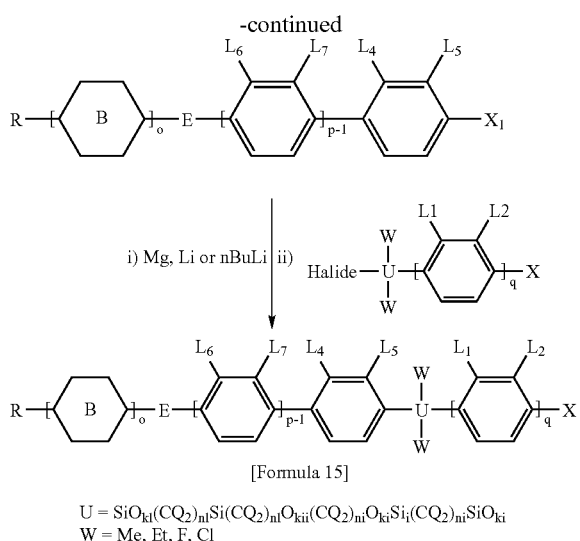

[Formula 15]

$U = SiO_{kl}(CQ_2)_{nl}Si(CQ_2)_{nl}O_{kii}(CQ_2)_{ni}O_{ki}Si_i(CQ_2)_{ni}SiO_{ki}$
$W = Me, Et, F, Cl$
$V = H, Me, Et, F, Cl, OMe, OEt$ In one embodiment of the method represented by Reaction Scheme 5, Pd-coupling reaction is performed by using a boronic acid derivative to provide a biphenyl or triphenyl derivative, which, in turn, is converted into an anion by using n-BuLi. Then, the resultant product is allowed to react with the silyl chloride to provide the silyl liquid crystal compound represented by formula 15.

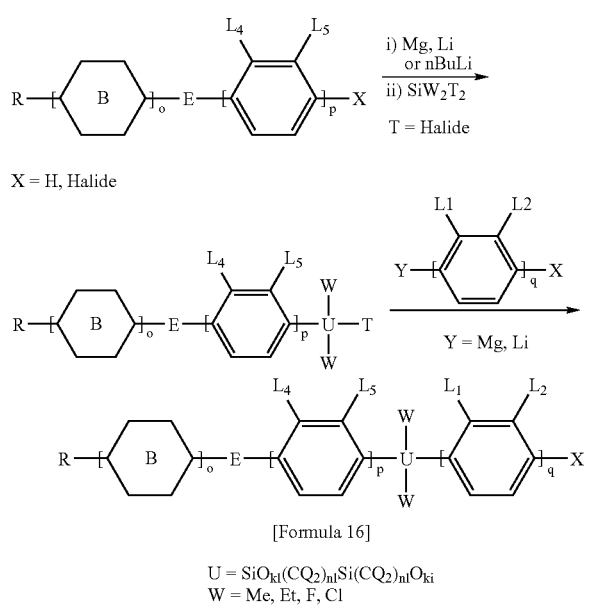

[Formula 16]

$U = SiO_{kl}(CQ_2)_{nl}Si(CQ_2)_{nl}O_{ki}$
$W = Me, Et, F, Cl$

In one embodiment of the method represented by Reaction Scheme 6, an excessive amount of $Me_2SiCl_2$ is added to the anion formed by Mg to provide the silyl chloride derivative, which, in turn, is allowed to react with a phenyl magnesium derivative to provide the silyl liquid crystal compound represented by formula 16.

In addition to the compounds obtained by way of the above Reaction Schemes 1~6, compounds obtained by similar methods or conventional methods known to one skilled in the art are also included in the scope of the present invention. The silicon-containing compounds obtained as described above may be mixed in an adequate ratio to provide a liquid crystal composition.

The present invention provides a liquid crystal composition, preferably a nematic liquid crystal composition, which comprises the silicon-containing compound represented by formula 1.

To provide the desired liquid crystal characteristics by a liquid crystal composition, about 5~20 components are generally used in combination in the liquid crystal composition. According to the present invention, it is possible to provide a liquid crystal composition having a low driving voltage and a fast response time by using the novel silicon-containing compound represented by formula 1, which can serve to impart high negative dielectric anisotropy as well as to reduce viscosity.

Although there is no particular limitation in the content of the compound represented by formula 1, more particularly at least one compound selected from the group consisting of the silicon-containing liquid crystal compounds represented by formulae 2~10, each compound is preferably used in an amount of 1~50 wt % based on 100 wt % of the total liquid crystal composition.

The liquid crystal composition according to the present invention may further comprise other liquid crystal compounds, currently used in a conventional liquid crystal composition, in addition to the silicon-containing compound represented by formula 1. Such compounds may be used in a controlled ratio, as necessary. Additionally, suitable additives may also be used, and such additives are disclosed in [H. Kelker/R. Hatz, Handbook of Liquid Crystals, Verlag Chemie, Weinheim, 1980]. For example, additives for modifying the dielectric anisotropy, viscosity and/or alignment of a nematic phase may be used. Particular examples of the additives that may be used in the liquid crystal composition according to the present invention include chiral dopants that inhibit the helical structure and reverse distortion of a liquid crystal, dichroic dyes, or the like.

The liquid crystal composition according to the present invention may be prepared by a method generally known to one skilled in the art. In one embodiment of such methods, various components that form the liquid crystal composition are dissolved at a temperature ranging from room temperature to a high temperature.

Also, the present invention provides a liquid display device, which comprises a liquid crystal layer obtained from the liquid crystal composition.

There is no particular limitation in the liquid crystal display device. Particular examples of the liquid crystal display device include display devices that require negative dielectric anisotropy, such as a vertical alignment liquid crystal display device, a patterned vertical alignment liquid crystal display device, superpatterned vertical alignment liquid crystal device, or the like.

The liquid crystal display device according to the present invention may be manufactured by a method generally known to one skilled in the art. One embodiment of such methods, a liquid crystal composition is dissolved at a suitable temperature, and then introduced into a liquid crystal device. The liquid crystal phase, dissolved as mentioned above, may be modified so that it can be applied for all types of liquid crystal display devices by virtue of the use of suitable additives.

BEST MODE FOR CARRYING OUT THE INVENTION

Reference will now be made in detail to the preferred embodiments of the present invention. It is to be understood that the following examples are illustrative only and the present invention is not limited thereto.

EXAMPLES 1~17

Example 1

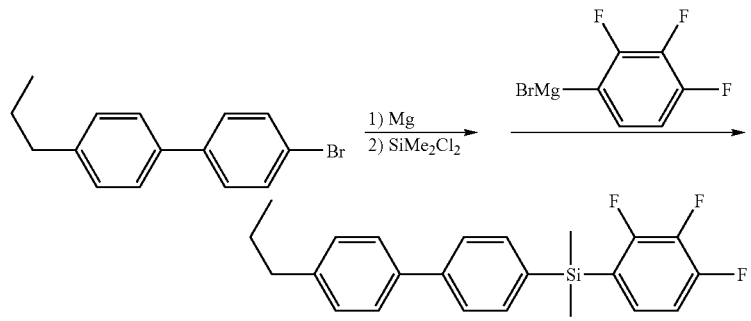

First, 500 mg of Mg was dissolved into dry THF, and a solution containing 5.6 g of 4-bromo-4'-n-propylbiphenyl dissolved in: 20 ml of dry THF was added gradually thereto to form a Grignard reagent. Next, 5.3 g of dichlorodimethylsilane was added thereto at 0° C., and the reaction mixture was allowed to react for about 3 hours. An excessive amount of hexane was added thereto, so that magnesium precipitate was formed. The precipitate was removed via filtration. After the analysis of the reaction product by NMR spectrometry, it was shown that mono-coupling compound and di-coupling compound was present in the ratio of about 90:10 (mono:di). When at least 2 equivalents of the silane compound are used at low temperature, it is possible to reduce the production of di-coupling compound to a ratio of 10% or less. In this case, it is possible to carry out subsequent steps with no separation of di-coupling compound. Then, a Grignard reagent was formed by using 2.1 g of 1-bromo-2,3,4-trifluorobenzene and 240 mg of Mg in 20 ml of dry THF. To the reagent, 3.4 g of the crude mono-coupling compound was added and the reaction mixture was heated to 60° C. After stirring for about 10 hours, the reaction mixture was worked up with water and hexane, and then purified by silica gel column chromatography to obtain the silicon-containing compound represented by the above formula (yield: 87%). 400 MHz $^1$H-NMR, CDCl$_3$, δ (ppm): 0.61 (s, 6H), 0.98 (t, 3H), 1.66~1.69 (m, 2H), 2.65 (t, 2H), 7.05 (m, 1H), 7.24 (d, 2H), 7.49 (m, 1H), 7.55~7.62 (m, 6H).

Example 2

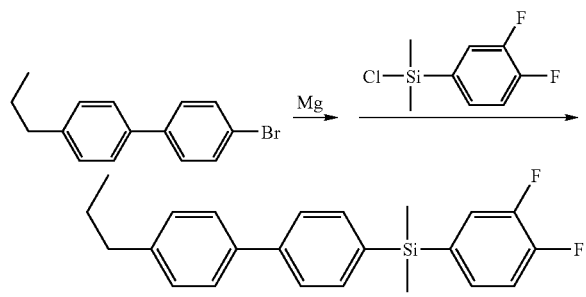

First, 1.0 equivalent of 1-bromo-3,4-difluorobenzene was dissolved into dry THF, and 1.1 equivalents of Mg were added thereto to form a Grignard reagent, which, in turn, was allowed to react with 2.0 equivalents of dichlorodimethylsilane. Next, chlorodimethyl(3,4-difluorophenyl)silane was obtained via vacuum distillation. Then, 255 mg of Mg was dissolved into 10 ml of dry THF, and a solution containing 2.80 g of 4-bromo-4'-n-propylbiphenyl dissolved in dry THF was added thereto to form a Grignard reagent. To the Grignard reagent, 2.17 g of the chlorodimethyl(3,4-difluorophenyl)silane obtained as described above was added at room temperature. After stirring for about 10 hours, the reaction mixture was worked up with water and hexane, and then purified by silica gel column chromatography to obtain the silicon-containing compound represented by the above formula (yield: 85%). 400 MHz $^1$H-NMR, CDCl$_3$, δ (ppm): 0.60 (s, 6H), 1.00 (t, 3H), 1.68~1.74 (m, 2H), 2.66 (t, 2H), 7.16~7.19 (m, 1H), 7.21~7.33 (m, 4H), 7.53~7.63 (m, 6H).

Example 3

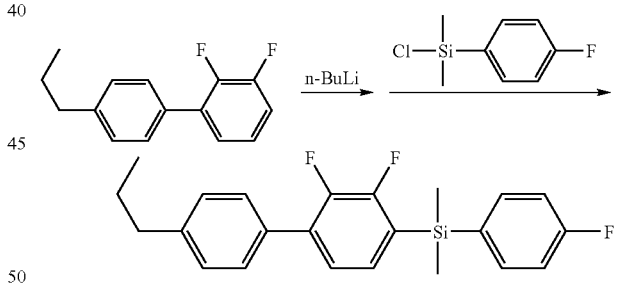

First, 1.0 equivalent of 1-bromo-4-fluorobenzene was dissolved into dry THF, and 1.1 equivalents of Mg were added thereto to form a Grignard reagent, which, in turn, was allowed to react with 2.0 equivalents of dichlorodimethylsilane. Next, chlorodimethyl(3,4-difluorophenyl)silane was obtained via vacuum distillation. Then, 3.24 g of 2,3-difluoro-4'-n-propylbiphenyl was dissolved into 20 ml of dry THF under nitrogen atmosphere, 7.3 ml of 2.0M n-BuLi was added to the solution at −78° C., and the reaction mixture was stirred sufficiently for about 3 hours to form an anion. To the anion, 2.64 g of the chlorodimethyl(4-fluorophenyl)silane obtained as described above was added, the reaction mixture was warmed to room temperature, and then stirred for about 1 hour. Then, the reaction mixture was worked up with water and hexane, and purified by silica gel column chromatography to obtain the silicon-containing compound represented by the above formula (yield: 91%). 400 MHz ¹H-NMR, CDCl₃, δ (ppm): 0.66 (s, 6H), 1.02 (t, 3H), 1.68~1.71 (m, 2H), 2.66 (t, 2H), 7.04~7.09 (m, 1H), 7.15 (dd, 2H), 7.19~7.23 (m, 1H), 7.29 (d, 2H), 7.48 (d, 2H), 7.61 (dd, 2H).

Example 4

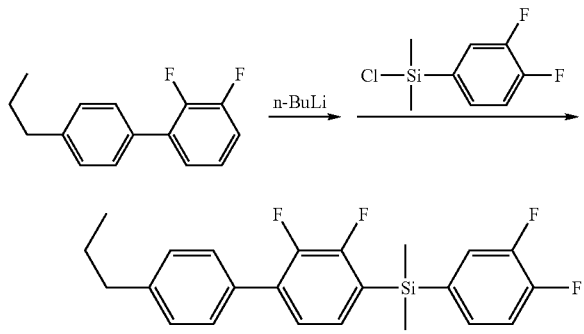

First, 6.40 g of 2,3-difluoro-4'-n-propylbiphenyl was dissolved into 30 ml of dry THF under nitrogen atmosphere, and 14.0 mL of 2.0M n-BuLi was added thereto at −78° C. Then the reaction mixture was stirred sufficiently for about 3 hours to form an anion. To the anion, 5.77 g of the chlorodimethyl (3,4-difluorophenyl)-silane obtained as described in Example 2 was added, the reaction mixture was warmed to room temperature and stirred for about 1 hour at room temperature. Then, the reaction mixture was worked up with water and hexane. Finally, the reaction product was purified by silica gel column chromatography to obtain the silicon-containing compound represented by the above formula (yield: 88%). 400 MHz ¹H-NMR, CDCl₃, δ (ppm): 0.63 (s, 6H), 1.05 (t, 3H), 1.71~1.86 (m, 2H), 2.77 (t, 2H), 7.12~7.21 (m, 1H), 7.29~7.35 (m, 2H), 7.38~7.49 (m, 3H), 7.55 (t, 1H), 7.62 (d, 2H).

Example 5

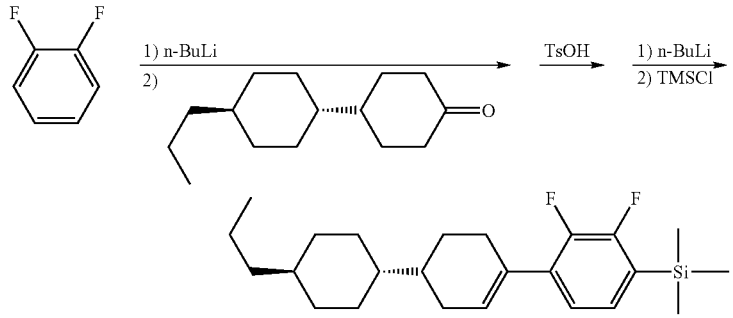

First, 1.20 g of 1,2-difluorobenzene was dissolved into 20 ml of dry THF under nitrogen atmosphere, 4.0 mL of 2.5M n-BuLi was added thereto at −78° C., and the reaction mixture was stirred for about 3 hours to form an anion. Next, 2.0 g of trans-cyclohexane was added thereto at low temperature, the reaction mixture was warmed to room temperature, and was stirred for about 2 hours at room temperature. Then, the reaction mixture was worked up with water and ether, and subjected to evaporation under reduced pressure to obtain a tertiary alcohol compound. The tertiary alcohol compound was dissolved into CH₂Cl₂ solvent, 500 mg of p-toluenesulfonic acid was added thereto, and the reaction mixture was stirred at 60° C. for 10 hours to carry out dehydration reaction. After cooling to room temperature, the reaction mixture was worked up with water and CH₂Cl₂, and was purified by silica gel column chromatography to obtain the cyclohexene compound with a yield of about 80%. Then, 2 g of the compound was dissolved into 10 ml of dry THF, 2.80 ml of 2.5M n-BuLi was added thereto at −78° C., and the reaction mixture was stirred for about 3 hours to form an anion. To the anion, 1.0 g of trimethylsilyl chloride was added at low temperature and was warmed gradually to room temperature. After stirring at room temperature for about 1 hour, the reaction mixture was worked up with water and hexane and purified by silica gel column chromatography to obtain the silicon-containing compound represented by the above formula (yield: 95%). 400 MHz ¹H-NMR, CDCl₃, δ (ppm): 0.33 (s, 9H), 0.91 (t, 3H), 0.93~1.11 (m, 4H), 1.12~1.24 (m, 3H), 1.24~1.53 (m, 6H), 1.72~1.88 (m, 3H), 1.88~2.05 (m, 2H), 2.21~2.29 (br, 1H), 2.29~2.52 (m, 2H), 5.98 (br, 1H), 6.95~7.04 (m, 2H).

Example 6

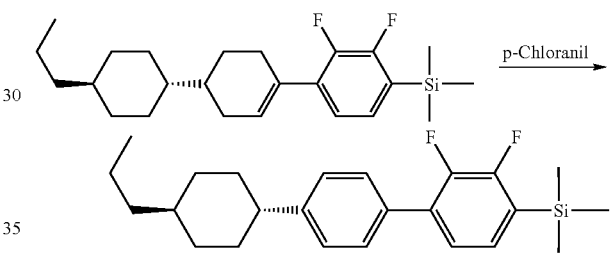

First, 2 g of the cyclohexene compound obtained from Example 5 was dissolved in 10 ml of xylene, 3.5 g of p-chloranil was added thereto, and the reaction mixture was heated at 150° C. for about 10 hours to perform a reaction. After cooling the reaction mixture to room temperature, hexane was added until the precipitate was formed. Then, the precipitate was filtered by using celite/silica gel. Finally, the reaction mixture was purified by silica gel column chromatography to obtain the silicon-containing compound represented by the above formula (yield: 83%). 400 MHz ¹H-NMR, CDCl₃, δ (ppm): 0.38 (s, 9H), 0.92 (t, 3H), 1.07~1.15 (m, 2H), 1.20~1.28 (m, 2H), 1.30~1.45 (m, 3H), 1.45~1.58 (m, 2H), 1.87~1.99 (br, 4H), 2.53 (t, 1H), 7.11~7.19 (m, 2H), 7.29 (d, 2H), 7.49 (d, 2H).

Example 7

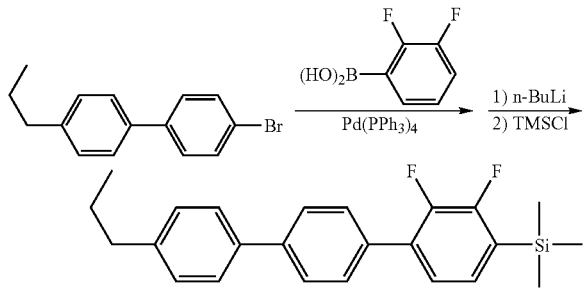

First, 3.0 g of 4-bromo-4'-n-propylbiphenyl was dissolved into 27 ml of DME, and 2.0 g of 2,3-difluorophenylboronic acid, 380 mg of tetrakis(triphenyl phosphine)palladium (0) and 27 ml of 2.0M $Na_2CO_3$ was added thereto. Next, the reaction mixture was heated to 100° C. to perform a reaction for about 10 hours. After checking complete disappearance of 4-bromo-4'-n-propylbiphenyl on TLC, the reaction mixture was cooled to room temperature, worked up with water and ether, and then purified by silica gel column chromatography to obtain the triphenyl compound with a yield of 90%. Then, 2.8 g of the triphenyl compound was dissolved into 10 ml of dry THF under nitrogen atmosphere, 4.3 ml of 2.5M n-BuLi was added thereto at −78° C. to form an anion over about 3 hours. Then 1.5 ml of TMSCl was added thereto, and the reaction mixture was warmed gradually to room temperature. After stirring at room temperature for about 1 hour, the reaction mixture was worked up with water and hexane, and then purified by silica gel column chromatography to obtain the silicon-containing compound represented by the above formula (yield: 96%). 400 MHz $^1$H-NMR, $CDCl_3$, δ (ppm): 0.39 (s, 9H), 1.04 (t, 3H), 1.66~1.76 (m, 2H), 2.66 (t, 2H), 7.18-7.21 (m, 1H), 7.21~7.28 (m, 1H), 7.31 (d, 2H), 7.58 (d, 2H), 7.64 (d, 2H), 7.70 (d, 2H)

Example 8

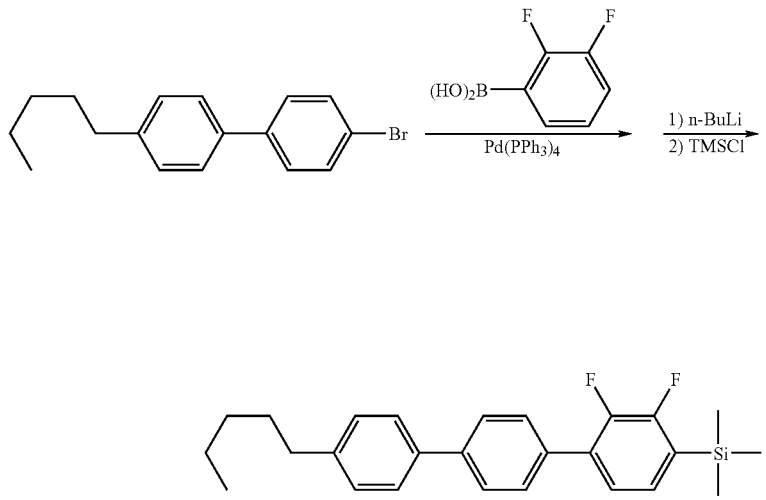

First, 4.8 g of 4-bromo-4'-n-pentylbiphenyl was added to 40 ml of DME, and 3.0 g of 2,3-difluorophenylboronic acid, 550 mg of tetrakis(triphenylphosphine)palladium(0) and 40 ml of 2.0M $Na_2CO_3$ was added thereto. Next, the reaction mixture was allowed to react for about 10 hours, while heating the reaction mixture at 100° C. The reaction mixture was cooled to room temperature and worked up with water and ether, and then purified by silica gel column chromatography to obtain the triphenyl compound with a yield of 88%. Then, 4.0 g of the triphenyl compound was dissolved into 20 ml of dry THF under nitrogen atmosphere, and 5.7 ml of 2.5M n-BuLi was added thereto to form an anion over about 3 hours. Then 2.0 ml of TMSCl was added thereto, and the reaction mixture was warmed gradually to room temperature. After stirring at room temperature for about 1 hour, the reaction mixture was worked up with water and hexane, and then purified by silica gel column chromatography to obtain the silicon-containing compound represented by the above formula (yield: 95%). 400 MHz $^1$H-NMR, $CDCl_3$, δ (ppm): 0.38 (s, 9H), 0.95 (m, 3H), 1.35~1.43 (m, 4H), 1.62~1.73 (m, 2H), 2.67 (t, 2H), 7.18~7.20 (m, 1H), 7.20~7.26 (m, 1H), 7.29 (d, 2H), 7.57 (d, 2H), 7.62 (d, 2H), 7.68 (d, 2H).

Example 9

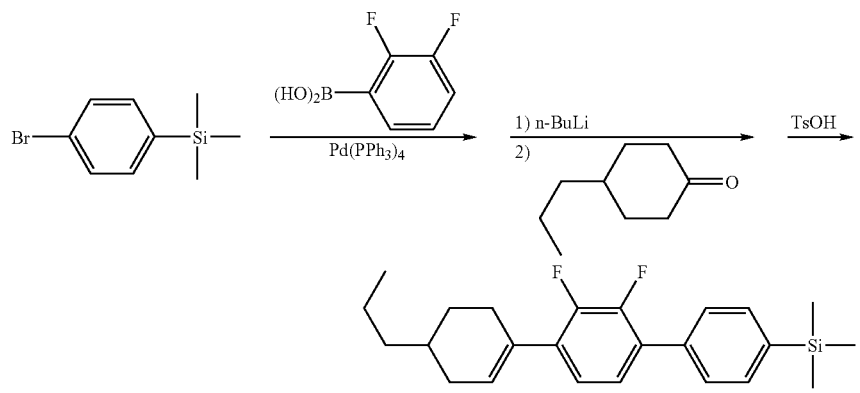

First, 7.9 g of 1-bromo-4-trimethylsilylbenzene was dissolved into 86 ml of DME, and 6.5 g of 2,3-difluorophenylboronic acid, 1.2 g of tetrakis(triphenylphosphine)palladium (0) and 86 ml of 2.0M $Na_2CO_3$ was added thereto. Next, the reaction mixture was heated to 100° C. to perform a reaction for about 10 hours. After being cooled to room temperature, the reaction mixture was worked up with water and ether, and then purified by silica gel column chromatography to obtain the 4'-trimethylsilyl-2,3-difluorobiphenyl compound with a yield of 91%. Then, 3.0 g of the biphenyl compound was dissolved into 20 ml of dry THF under nitrogen atmosphere, and 5.0 ml of 2.5M n-BuLi was added thereto at −78° C. to form an anion over about 3 hours. Then, 2.0 ml of 4-n-propylcyclohexanone was added to the anion, and the reaction mixture was warmed gradually to room temperature. After stirring at room temperature for 2 hours, the reaction mixture was worked up with water and ether, and evaporated under reduced pressure, and then dissolved into $CH_2Cl_2$ solvent. Next, 1.0 g of TsOH was added thereto, and the reaction mixture was allowed to react at 60° C. for 10 hours. After the completion of the reaction, the reaction mixture was purified by silica gel column chromatography to obtain the silicon-containing compound (yield: 80%). 400 MHz $^1$H-NMR, $CDCl_3$, δ (ppm): 0.38 (s, 9H), 0.97 (m, 3H), 1.34~1.46 (m, 5H), 1.63~1.76 (br, 1H), 1.84~1.98 (m, 2H), 2.33~2.59 (m, 3H), 6.06 (br, 1H), 7.05~7.12 (m, 1H), 7.12~7.18 (m, 1H), 7.56 (d, 2H), 7.63 (d, 2H).

Example 10

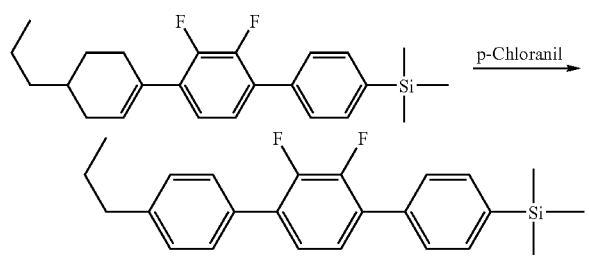

First, 2.5 g of the cyclohexene compound obtained from Example 9 was dissolved in 10 ml of xylene, 4.0 g of p-chloranil was added thereto, and the reaction mixture was heated at 150° C. for about 10 hours to perform a reaction. After cooling the reaction mixture to room temperature, hexane was added until the precipitate was formed. Then, the precipitate was filtered by using celite/silica gel. Finally, the reaction mixture was purified by silica gel column chromatography to obtain the silicon-containing compound represented by the above formula (yield: 85%). 400 MHz $^1$H-NMR, $CDCl_3$, δ (ppm) 0.36 (s, 9H), 1.02 (t, 3H), 1.69~1.78 (m, 2H), 2.69 (t, 2H), 7.21~7.28 (m, 2H), 7.30 (d, 2H), 7.54 (d, 2H), 7.63 (d, 2H), 7.68 (d, 2H).

Example 11

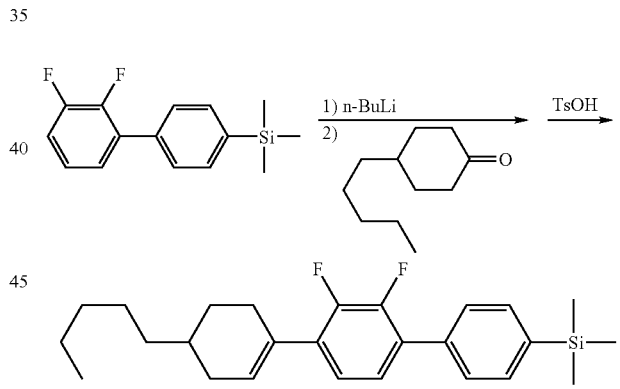

First, 3.48 g of 4'-trimethylsilyl-2,3-difluorobiphenyl was dissolved into 20 ml of dry THF, and 5.8 ml of 2.5M n-BuLi was added thereto at −78° C. to form an anion over about 3 hours. Next, 2.8 ml of 4-n-pentylcyclohexanone was added thereto and the reaction mixture was warmed gradually to room temperature. The reaction mixture was stirred at room temperature for about 2 hours, worked up with water and ether, and evaporated under reduced pressure. Then, the reaction mixture was dissolved into $CH_2Cl_2$ solvent, 1.0 g of TsOH was added thereto, and the reaction mixture was allowed to react at 60° C. for about 10 hours. After the completion of the reaction, the reaction mixture was purified by silica gel column chromatography to obtain the silicon-containing compound represented by the above formula (yield: 82%). 400 MHz $^1$H-NMR, $CDCl_3$, δ (ppm): 0.33 (s, 9H), 0.93 (m, 3H), 1.29~1.53 (m, 9H), 1.60~1.71 (br, 1H), 1.81~1.97 (m, 2H), 2.34~2.50 (m, 3H), 6.04 (br, 1H), 7.03~7.102 (m, 1H), 7.10~7.16 (m, 1H), 7.55 (d, 2H), 7.62 (d, 2H).

Example 12

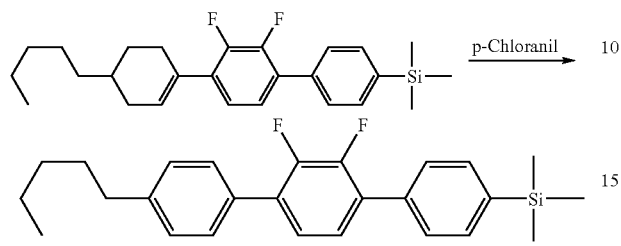

First, 2.3 g of the cyclohexene compound obtained from Example 9 was dissolved in 10 ml of xylene, 4.1 g of p-chloranil was added thereto, and the reaction mixture was heated at 150° C. for about 10 hours to perform a reaction. After cooling the reaction mixture to room temperature, hexane was added until the precipitate was formed. Then, the precipitate was filtered by using celite/silica gel. Finally, the reaction mixture was purified by silica gel column chromatography to obtain the silicon-containing compound represented by the above formula (yield: 83%). 400 MHz $^1$H-NMR, CDCl$_3$, δ (ppm): 0.33 (s, 9H), 0.92~0.95 (m, 3H), 1.36~1.41 (m, 4H), 1.65~1.74 (m, 2H), 2.68 (t, 2H), 7.24~7.27 (m, 2H), 7.30 (d, 2H), 7.52 (d, 2H), 7.59 (d, 2H), 7.64 (d, 2H).

Example 13

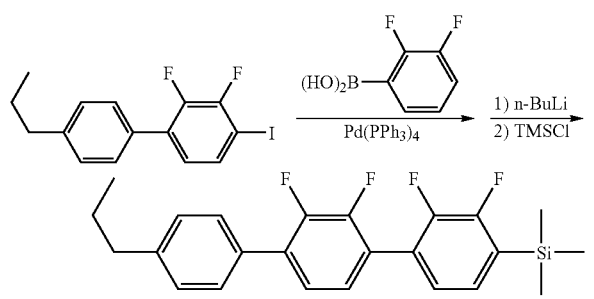

First, 7.28 g of 2,3-difluoro-4-iodo-4'-n-pentylbiphenyl was dissolved into 50 ml of DME as a solvent. Next, 3.85 g of 2,3-difluorophenylboronic acid, 705 mg of tetrakis(triphenylphosphine)palladium(0) and 50 ml of 2.0M Na$_2$CO$_3$ was added thereto, and the reaction mixture was heated at 100° C. for about 10 hours. After being cooled to room temperature, the reaction mixture was worked up with water and hexane, and purified by silica gel column chromatography to obtain the triphenyl compound with a yield of 70%. Then, 2.2 g of the triphenyl compound was dissolved into 10 ml of dry THF under nitrogen atmosphere, and 3.1 ml of 2.5M n-BuLi was added at −78° C. to form an anion over about 3 hours. Then, 1.0 ml of TMSCl was added thereto and the reaction mixture was warmed gradually to room temperature. After being stirred at room temperature for about 1 hour, the reaction mixture was worked up with water and hexane, and then purified by silica gel column chromatography to obtain the silicon-containing compound represented by the above formula (yield: 90%). 400 MHz $^1$H-NMR, CDCl$_3$, δ (ppm): 0.39 (s, 9H), 1.00 (m, 3H), 1.67~1.74 (m, 2H), 2.67 (t, 2H), 7.16~7.22 (m, 2H), 7.27~7.32 (m, 4H), 7.52 (d, 2H).

Example 14

Liquid Crystal Composition (1)

A liquid crystal composition was prepared from the materials as shown in the following Table 1. In Table 1, each percent ratio refers to parts by weight per hundred parts of composition.

TABLE 1

| COMPOUND AND CONTENT | |
|---|---|
| (structure) | 18% |
| (structure) | 18% |
| (structure) | 16% |
| (structure) | 16% |
| (structure) | 12% |
| (structure) | 8% |
| (structure) | 6% |
| (structure) | 3% |

TABLE 1-continued

| COMPOUND AND CONTENT | |
|---|---|
| [structure: pentyl-cyclohexyl-difluorophenyl-phenyl-Si(CH3)3] | 3% |

Example 15

Liquid Crystal Composition (2)

A liquid crystal composition was prepared from the materials as shown in the following Table 2. In Table 2, each percent ratio refers to parts by weight per hundred parts of composition.

TABLE 2

| COMPOUND AND CONTENT | |
|---|---|
| [structure: propyl-phenyl-difluorophenyl-phenyl-Si] | 22% |
| [structure: pentyl-phenyl-difluorophenyl-phenyl-Si] | 22% |
| [structure: propyl-phenyl-difluorophenyl-difluorophenyl-Si] | 12% |
| [structure: propyl-cyclohexyl-cyclohexyl-difluorophenyl-Si] | 8% |
| [structure: propyl-cyclohexyl-difluorophenyl-phenyl-Si] | 6% |
| [structure: propyl-phenyl-phenyl-difluorophenyl-Si] | 6% |
| [structure: pentyl-phenyl-phenyl-difluorophenyl-Si] | 6% |

TABLE 2-continued

| COMPOUND AND CONTENT | |
|---|---|
| [structure: propyl-cyclohexyl-phenyl-difluorophenyl-Si] | 5% |
| [structure: pentyl-cyclohexyl-difluorophenyl-phenyl-Si] | 5% |
| [structure: propyl-phenyl-phenyl-Si-trifluorophenyl] | 4% |
| [structure: propyl-phenyl-trifluorophenyl-Si-difluorophenyl] | 4% |

Example 16

Liquid Crystal Composition (3)

A liquid crystal composition was prepared from the materials as shown in the following Table 3. In Table 3, each percent ratio refers to parts by weight per hundred parts of composition.

TABLE 3

| COMPOUND AND CONTENT | |
|---|---|
| [structure: propyl-phenyl-difluorophenyl-phenyl-Si] | 16% |
| [structure: pentyl-phenyl-difluorophenyl-phenyl-Si] | 16% |
| [structure: propyl-phenyl-difluorophenyl-difluorophenyl-Si] | 13% |
| [structure: propyl-phenyl-phenyl-difluorophenyl-Si] | 12% |

TABLE 3-continued

COMPOUND AND CONTENT

[Structure: biphenyl-difluorophenyl-Si, 12%]

[Structure: cyclohexyl-difluorophenyl-phenyl-Si, 10%]

[Structure: cyclohexyl-phenyl-difluorophenyl-Si, 10%]

[Structure: bicyclohexyl-difluorophenyl-Si, 5%]

[Structure: biphenyl-Si-fluorophenyl, 3%]

[Structure: difluorobiphenyl-Si-fluorophenyl, 3%]

EXPERIMENTAL EXAMPLE 1

Evaluation for Physical Properties of Liquid Crystal Composition

The liquid crystal compositions according to the present invention were evaluated for their physical properties according to the following test.

The liquid crystal compositions according to Examples 14~16 were used. Each composition was introduced into a test tube in an amount of 1 g under the nitrogen atmosphere, and then heated at 150° C. for 2 hours to measure the phase transition temperature. Herein, clearing point (c.p.) of each composition refers to the isotropic liquid phase transition temperature in a nematic phase. Additionally, optical anisotropy (Δn) of each composition was measured at 20° C./589 nm, while dielectric anisotropy (Δε) of each composition was measured at 20° C./1 kHz. Also, rotational viscosity ($\gamma_1$) of each composition was measured at 20° C. The results are shown in the following Table 4.

After the test, it can be seen that the liquid crystal compositions according to Examples 14~16, which comprise, as an active component, the novel silicon-containing compound represented by formula 1 according to the present invention, show high negative (−) dielectric anisotropy and low viscosity (see Table 4).

TABLE 4

| Ex. | Clearing point (° C.) | Optical anisotropy | Dielectric anisotropy | Viscosity (mPas) |
|---|---|---|---|---|
| 14 | 98 | 0.127 | −5.9 | 112 |
| 15 | 91 | 0.116 | −5.7 | 94 |
| 16 | 102 | 0.099 | −5.8 | 105 |

INDUSTRIAL APPLICABILITY

As can be seen from the foregoing, the present invention provides a novel nematic liquid crystal compound, which has low viscosity and high negative dielectric anisotropy, and a liquid crystal composition comprising the same compound. According to the present invention, it is possible to provide a liquid crystal display device that satisfies various desired characteristics, including a fast response time and a low driving voltage.

While this invention has been described in connection with what is presently considered to be the most practical and preferred embodiment, it is to be understood that the invention is not limited to the disclosed embodiment and the drawings. On the contrary, it is intended to cover various modifications and variations within the spirit and scope of the appended claims.

The invention claimed is:

1. A silicon-containing compound represented by the following formula 1:

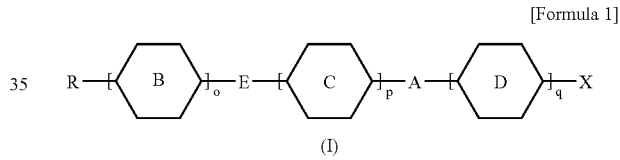

(I)

[Formula 1]

wherein A is selected from the group consisting of
$SiMe_2O_{k1}(CQ_2)_{n1}$, $SiEt_2O_{k1}(CQ_2)_{n1}$, $SiF_2O_{k1}(CQ_2)_{n1}$, $SiCl_2O_{k1}(CQ_2)_{n1}$, $SiMe_2(CQ_2)_{n1}O_{k1}$, $SiEt_2(CQ_2)_{n1}O_{k1}$, $SiF_2(CQ_2)_{n1}O_{k1}$, $SiCl_2(CQ_2)_{n1}O_{k1}$, $O_{k1}SiMe_2(CQ_2)_{n1}$, $O_{k1}SiEt_2(CQ_2)_{n1}$, $O_{k1}\ SiF_2(CQ_2)_{n1}$, $O_{k1}SiCl_2(CQ_2)_{n1}$, $(CQ_2)_{n1}O_{k1}SiMe_2$, $(CQ_2)_{n1}O_{k1}SiEt_2$, $(CQ_2)_{n1}O_{k1}SiF_2$, $(CQ_2)_{n1}O_{k1}SiCl_2$, $O_{k1}(CQ_2)_{n1}SiMe_2$, $O_{k1}(CQ_2)_{n1}SiEt_2$, $O_{k1}(CQ_2)_{n1}\ SiF_2$, $O_{k1}(CQ_2)_{n1}SiCl_2$, $(CQ_2)_{n1}SiMe_2O_{k1}$, $(CQ_2)_{n1}\ SiEt_2O_{k1}$, $(CQ_2)_{n1}SiF_2O_{k1}$, $(CQ_2)_{n1}SiCl_2O_{k1}$, $(CH_2)_{n1}$, CH=CH, C≡C, O, S, COO, OCO, $CF_2O$, $OCF_2$, OCOO, $CH_2O$, $CH_2CO$, $OCH_2$ and $COCH_2$, wherein $k_1$ is 0 or 1, Q is H or F, $n_1$ is an integer between 0 and 3, where $k_1$=0, $n_1$=0~2 and where $k_1$=1, p>0;

ring B is selected from the group consisting of

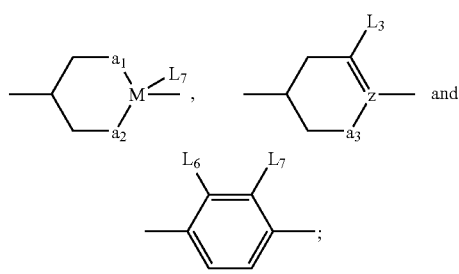

and ring C is selected from the group consisting of

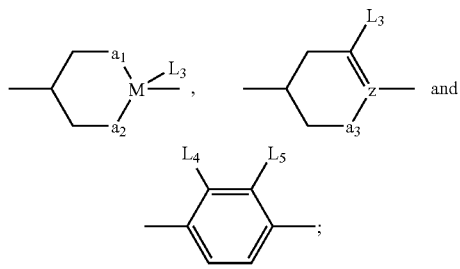

ring D is selected from the group consisting of

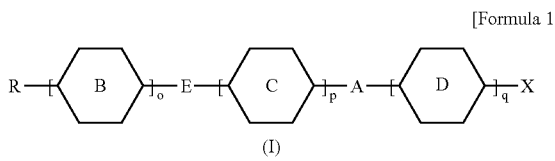

[Formula 1]

$$R-[B]_o-E-[C]_p-A-[D]_q-X$$

(I)

wherein the substituents, which are introduced into ring B, ring C or ring D and represented by $L_1$ to $L_7$, are independent from each other, even if they have the same designations;

M is selected from C, and N, with the proviso that if M is N, $L_3$ or $L_7$ is null;

Z is C;

each of $a_1$, $a_2$ and $a_3$ is independently selected from C, and NR;

E is selected from the group consisting of $SiMe_2O_{k2}(CQ_2)_{n2}$, $SiEt_2O_{k2}(CQ_2)_{n2}$, $SiF_2O_{k2}(CQ_2)_{n2}$, $SiCl_2O_{k2}(CQ_2)_{n2}$, $SiMe_2(CQ_2)_{n2}O_{k2}$, $SiEt_2(CQ_2)_{n2}O_{k2}$, $SiF_2(CQ_2)_{n2}O_{k2}$, $SiCl_2(CQ_2)_{n2}O_{k2}$, $O_{k2}SiMe_2(CQ_2)_{n2}$, $O_{k2}SiEt_2(CQ_2)_{n2}$, $O_{k2}SiF_2(CQ_2)_{n2}$, $O_{k2}SiCl_2(CQ_2)_{n2}$, $(CQ_2)_{n2}O_{k2}SiMe_2$, $(CQ_2)_{n2}O_{k2}SiEt_2$, $(CQ_2)_{n2}O_{k2}SiF_2$, $(CQ_2)_{n2}O_{k2}SiCl_2$, $O_{k2}(CQ_2)_{n2}SiMe_2$, $O_{k2}(CQ_2)_{n2}SiEt_2$, $O_{k2}(CQ_2)_{n2}SiF_2$, $O_{k2}(CQ_2)_{n2}SiCl_2$, $(CQ_2)_{n2}SiMe_2O_{k2}$, $(CQ_2)_{n2}SiEt_2O_{k2}$, $(CQ_2)_{n2}SiF_2O_{k2}$, $(CQ_2)_{n2}SiCl_2O_{k2}$, $(CH2)_{n2}$, $C\equiv C$, O, S, COO, OCO, $CF_2O$, $OCF_2$, OCOO, $CH_2O$, $CH_2CO$, $OCH_2$ and $COCH_2$, wherein $k_2$ is 0 or 1, Q is H or F, and $n_2$ is an integer between 0 and 3, where $k_2=0$, $n_2=0\sim2$ and where $k_2=1$, $p>0$;

R is selected from the group consisting of H, a $C_1\sim C_{15}$ alkyl group, and a $C_2\sim C_{15}$ alkene group, wherein the alkene group is $CH=CH_2$, $CH=CHCH_3$ (E,Z), $CH_2CH=CH_2$, $CH=CHCH_2CH_3$ (E,Z), $CH_2CH=CHCH_3$ (E,Z), $CH_2CH_2CH=CH_2$, $CH=CHCH_2CH_2CH_3$ (E,Z), $CH_2CH=CHCH_2CH_3$ (E,Z), $CH_2CH_2CH=CHCH_3$ (E,Z) or $CH_2CH_2CH_2CH=CH_2$;

$R_1$ is selected from the group consisting of H, a $C_1\sim C_{15}$ alkyl group and a $C_2\sim C_{15}$ alkene group, wherein the alkene group is $CH=CH_2$, $CH=CHCH_3$ (E,Z), $CH_2CH=CH_2$, $CH=CHCH_2CH_3$ (E,Z), $CH_2CH=CHCH_3$ (E,Z), $CH_2CH_2CH=CH_2$, $CH=CHCH_2CH_2CH_3$ (E,Z), $CH_2CH=CHCH_2CH_3$ (E,Z), $CH_2CH_2CH=CHCH_3$ (E,Z) or $CH_2CH_2CH_2CH=CH_2$;

X is selected from the group consisting of H, $SiR_2R_3R_4$, $CF_3$, $OCF_3$, CN, NCS, halogen atoms, and an alkoxy group ($OR_1$);

each of $R_2$, $R_3$ and $R_4$ is independently selected from R and halogen atoms;

each of $L_1$, $L_2$, $L_3$, $L_4$, $L_5$, $L_6$ and $L_7$ is independently selected from the group consisting of H, halogen atoms, CN, $CF_3$, $OCF_3$ and NCS;

each of o, p and q independently represents an integer between 0~2, and $o+p+q\geq 2$, where when $k_1$ and/or $k_2=0$, each of o, p, q=1~2; and at least one of E, A and X contains silicon.

2. The silicon-containing compound according to claim 1, which has negative dielectric anisotropy.

3. The silicon-containing compound according to claim 1, which is a compound represented by any one formula selected from the group consisting of formula 2~formula 10:

[Formula 2]

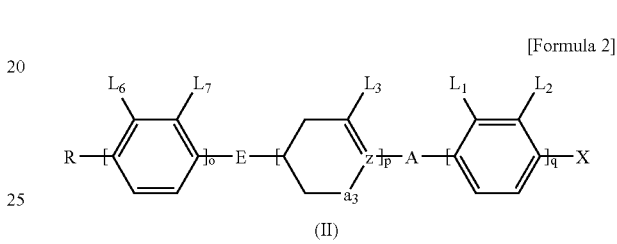

(II)

[Formula 3]

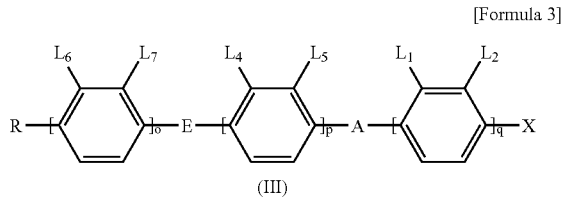

(III)

[Formula 4]

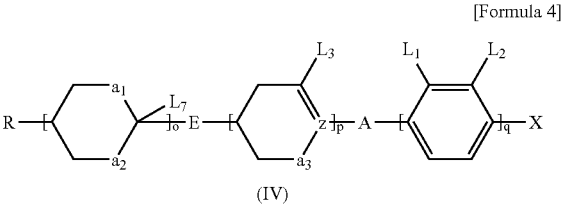

(IV)

[Formula 5]

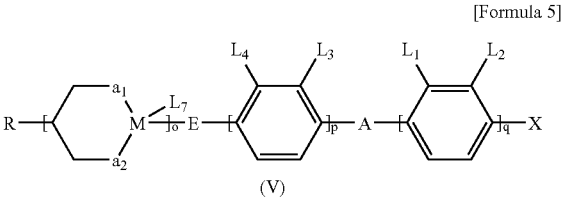

(V)

[Formula 6]

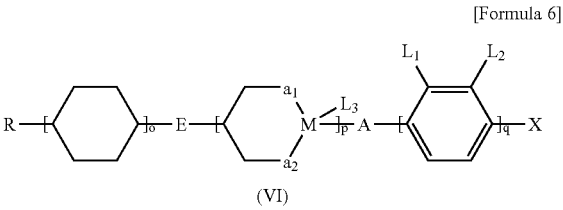

(VI)

[Formula 7]

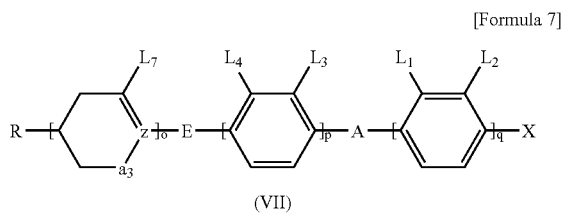

(VII)

-continued

[Formula 8]

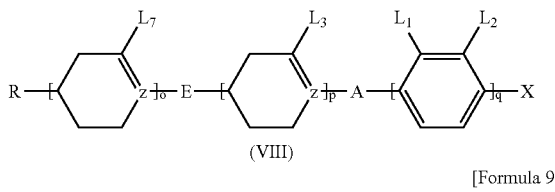

(VIII)

[Formula 9]

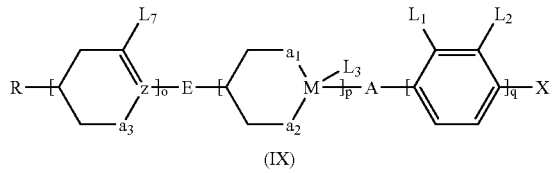

(IX)

[Formula 10]

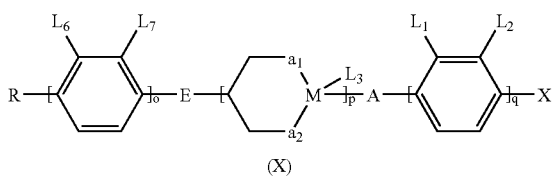

(X)

wherein A is selected from the group consisting of $SiMe_2O_{k1}(CQ_2)_{n1}$, $SiEt_2O_{k1}(CQ_2)_{n1}$, $SiF_2O_{k1}(CQ_2)_{n1}$, $SiCl_2O_{k1}(CQ_2)_{n1}$, $SiMe_2(CQ_2)_{n1}O_{k1}$, $SiEt_2(CQ_2)_{n1}O_{k1}$, $SiF_2(CQ_2)_{n1}O_{k1}$, $SiCl_2(CQ_2)_{n1}O_{k1}$, $O_{k1}SiMe_2(CQ_2)_{n1}$, $O_{k1}SiEt_2(CQ_2)_{n1}$, $O_{k1}SiF_2(CQ_2)_{n1}$, $O_{k1}SiCl_2(CQ_2)_{n1}$, $(CQ_2)_{n1}O_{k1}SiMe_2$, $(CQ_2)_{n1}O_{k1}SiEt_2$, $(CQ_2)_{n1}O_{k1}SiF_2$, $(CQ_2)_{n1}O_{k1}SiCl_2$, $O_{k1}(CQ_2)_{n1}SiMe_2$, $O_{k1}(CQ_2)_{n1}SiEt_2$, $O_{k1}(CQ_2)_{n1}SiF_2$, $O_{k1}(CQ_2)_{n1}SiCl_2$, $(CQ_2)_{n1}SiMe_2O_{k1}$, $(CQ_2)_{n1}SiEt_2O_{k1}$, $(CQ_2)_{n1}SiF_2O_{k1}$, $(CQ_2)_{n1}SiCl_2O_{k1}$, $(CH_2)_{n1}$, $CH=CH$, $C\equiv C$, O, S, COO, OCO, $CF_2O$, $OCF_2$, OCOO, $CH_2O$, $CH_2CO$, $OCH_2$ and $COCH_2$, wherein $k_1$ is 0 or 1, Q is H or F, $n_1$ is an integer between 0 and 3 where $k_1=0$, $n_1=0\sim2$ and where $k_1=1$, p>0;

M is selected from C, and N, with the proviso that if M is N, $L_3$ or $L_7$ is null;

Z is C;

each of $a_1$, $a_2$ and $a_3$ is independently selected from C, and NR;

E is selected from the group consisting of $SiMe_2O_{k2}(CQ_2)_{n2}$, $SiEt_2O_{k2}(CQ_2)_{n2}$, $SiF_2O_{k2}(CQ_2)_{n2}$, $SiCl_2O_{k2}(CQ_2)_{n2}$, $SiMe_2(CQ_2)_{n2}O_{k2}$, $SiEt_2(CQ_2)_{n2}O_{k2}$, $SiF_2(CQ_2)_{n2}O_{k2}$, $SiCl_2(CQ_2)_{n2}O_{k2}$, $O_{k2}SiMe_2(CQ_2)_{n2}$, $O_{k2}SiEt_2(CQ_2)_{n2}$, $O_{k2}SiF_2(CQ_2)_{n2}$, $O_{k2}SiCl_2(CQ_2)_{n2}$, $(CQ_2)_{n2}O_{k2}SiMe_2$, $(CQ_2)_{n2}O_{k2}SiEt_2$, $(CQ_2)_{n2}O_{k2}SiF_2$, $(CQ_2)_{n2}O_{k2}SiCl_2$, $O_{k2}(CQ_2)_{n2}SiMe_2$, $O_{k2}(CQ_2)_{n2}SiEt_2$, $O_{k2}(CQ_2)_{n2}SiF_2$, $O_{k2}(CQ_2)_{n2}SiCl_2$, $(CQ_2)_{n2}SiMe_2O_{k2}$, $(CQ_2)_{n2}SiEt_2O_{k2}$, $(CQ_2)_{n2}SiF_2O_{k2}$, $(CQ_2)_{n2}SiCl_2O_{k2}$, $(CH_2)_{n2}$, $C\equiv C$, O, S, COO, OCO, $CF_2O$, $OCF_2$, OCOO, $CH_2O$, $CH_2CO$, $OCH_2$ and $COCH_2$, wherein $k_2$ is 0 or 1, Q is H or F, and $n_2$ is an integer between 0 and 3, where $k_2=0$, $n_2=0\sim2$ and where $k_2=1$, p>0;

R is selected from the group consisting of H, a $C_1\sim C_{15}$ alkyl group, and a $C_2\sim C_{15}$ alkene group, wherein the alkene group is $CH=CH_2$, $CH=CHCH_3$ (E,Z), $CH_2CH=CH_2$, $CH=CHCH_2CH_3$ (E,Z), $CH_2CH=CHCH_3$ (E,Z), $CH_2CH_2CH=CH_2$, $CH=CHCH_2CH_2CH_3$ (E,Z), $CH_2CH=CHCH_2CH_3$ (E,Z), $CH_2CH_2CH=CHCH_3$ (E,Z) or $CH_2CH_2CH_2CH=CH_2$;

$R_1$ is selected from the group consisting of H, a $C_1\sim C_{15}$ alkyl group and a $C_2\sim C_{15}$ alkene group, wherein the alkene group is $CH=CH_2$, $CH=CHCH_3$ (E,Z), $CH_2CH=CH_2$, $CH=CHCH_2CH_3$ (E,Z), $CH_2CH=CHCH_3$ (E,Z), $CH_2CH_2CH=CH_2$, $CH=CHCH_2CH_2CH_3$ (E,Z), $CH_2CH=CHCH_2CH_3$ (E,Z), $CH_2CH_2CH=CHCH_3$ (E,Z) or $CH_2CH_2CH_2CH=CH_2$;

X is selected from the group consisting of H, $SiR_2R_3R_4$, $CF_3$, $OCF_3$, CN, NCS, halogen atoms, and an alkoxy group ($R_1O$);

each of $R_2$, $R_3$ and $R_1$ is independently selected from R and halogen atoms;

each of $L_1$, $L_2$, $L_3$, $L_4$, $L_5$, $L_6$ and $L_7$ is independently selected from the group consisting of H, halogen atoms, CN, $CF_3$, $OCF_3$ and NCS; and each of o, p and q independently represents an integer between 0~2, and o+p+q>2, and where $k_1$ and/or $k_2=0$, each of o, p, q=1~2.

4. The silicon-containing compound according to claim 1, which is selected from the group consisting of the following compounds:

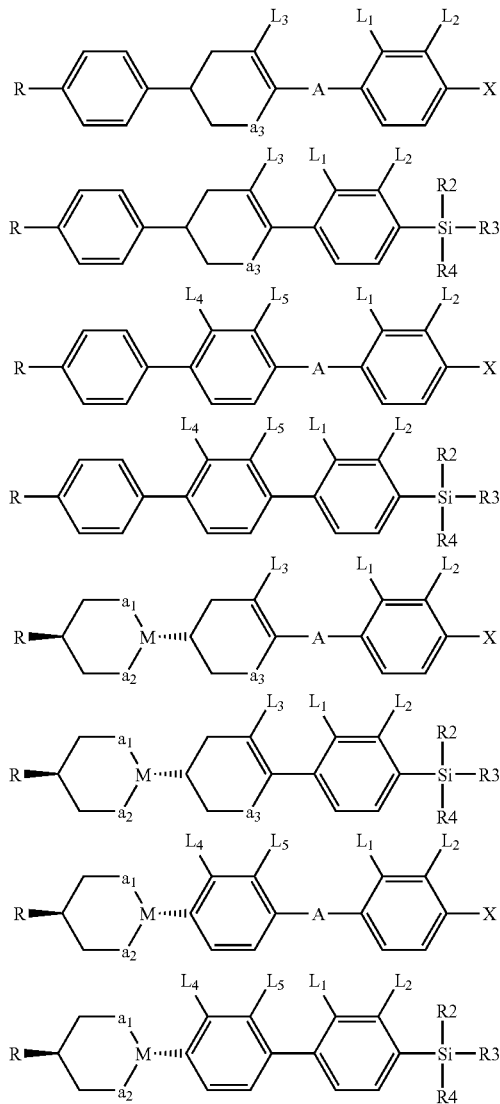

-continued

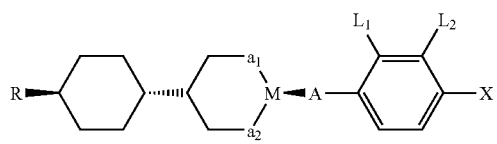

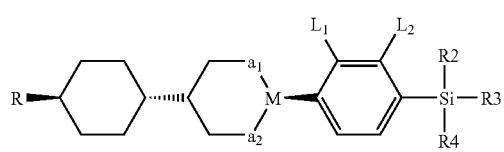

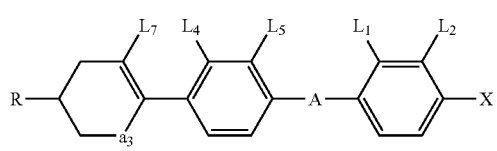

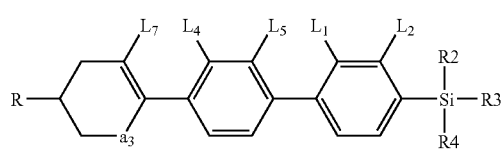

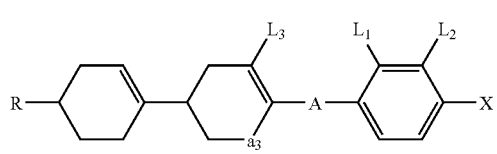

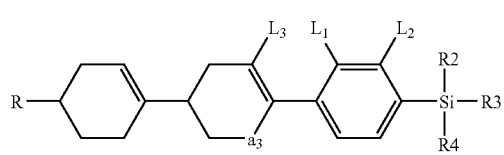

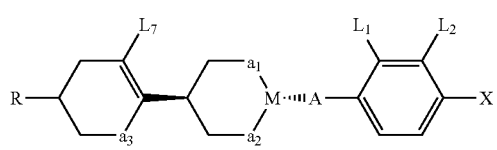

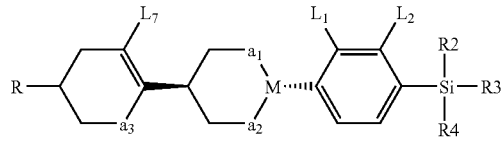

-continued

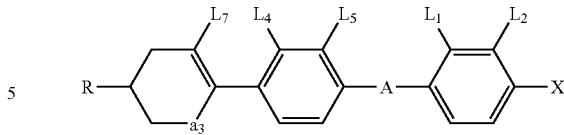

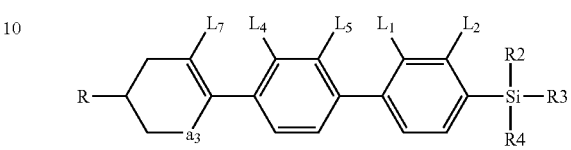

wherein A is selected from the group consisting of $SiO_{k1}(CQ_2)_{n1}$, $Si(CQ_2)_{n1}O_{k1}$, $(CQ_2)_{n1}O_{k1}Si$, $(CQ_2)_{n1}SiO_{k1}$, $O_{k1}(CQ_2)_{n1}Si$ and $O_{k1}Si(CQ_2)_{n1}$, and $k_1$, Q, $n_1$, R, $R_2$, $R_3$, $R_1$, M, $a_1$, $a_2$, $a_3$, $L_1$, $L_2$, $L_3$, $L_4$, $L_5$, $L_7$, and X are the same as defined in claim 1.

5. The silicon-containing compound as claimed in claim 1, which has stereoisomers.

6. The silicon-containing compound as claimed in claim 5, wherein the stereoisomers of the silicon-containing compound are present in a ratio of trans-isomer:cis-isomer of 85~100:15~0.

7. A liquid crystal composition, which comprises at least one silicon-containing compound represented by the following formula 1 as defined in claim 1:

[Formula 1]

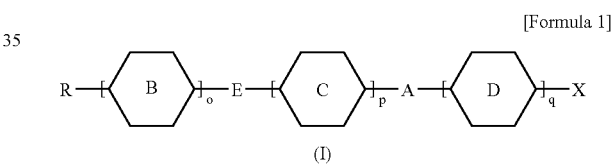

(I)

wherein ring B, ring C, ring D, A, E, Z, R, $R_1$, $R_2$, $R_3$, $R_4$, M, $a_1$, $a_2$, $a_3$, $L_1$, $L_2$, $L_3$, $L_4$, $L_5$, $L_6$, $L_7$, X, o, p and q are the same as defined in claim 1.

8. The liquid crystal composition as claimed in claim 7, wherein each silicon-containing compound has negative dielectric anisotropy.

9. The liquid crystal composition as claimed in claim 7, wherein each silicon-containing compound has stereoisomers.

10. The liquid crystal composition as claimed in claim 9, wherein the stereoisomers of the silicon-containing compound are present in a ratio of trans-isomer:cis-isomer of 85~100:15~0.

11. The liquid crystal composition as claimed in claim 7, wherein each silicon-containing compound is present in an amount of 1~50 wt % based on 100 wt % of the total weight of the composition.

12. A liquid crystal display device, which comprises a liquid crystal layer prepared from the liquid crystal composition as defined in claim 7.

13. A method for preparing a silicon-containing compound as claimed in claim 1, which is represented by the following Reaction Scheme 1:

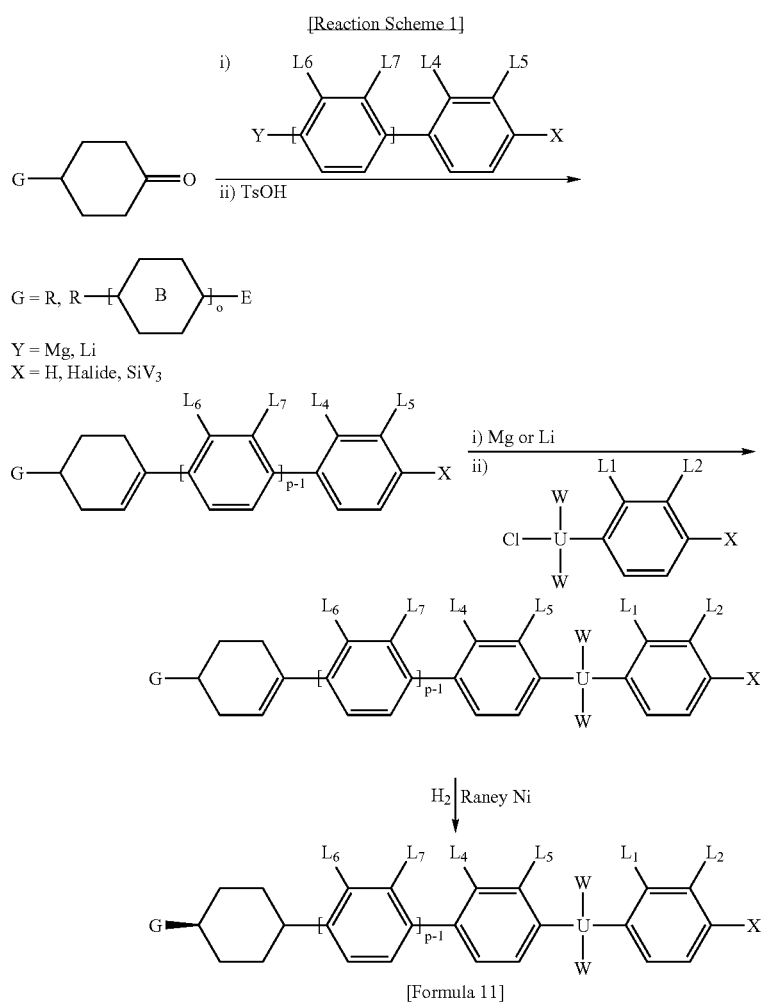

wherein U is selected from $SiO_{k1}(CQ_2)_{n1}$, $Si(CQ_2)_{n1}O_{k1}$, $(CQ_2)_{n1}O_{k1}Si$, and $(CQ_2)_{n1}SiO_{k1}$, wherein $k_1$ is 0 or 1, Q is H or F, and $n_1$ is an integer between 0 and 3, where $k_1=0$, $n_1=0\sim2$ and where $k_1=1$, $p>0$;

W is selected from Me, Et, F and Cl; and ring B, R, E, X, $L_1$, $L_2$, $L_4$, $L_5$, $L_6$, $L_7$, o, and p are the same as defined in claim 1.

14. A method for preparing a silicon-containing compound as claimed in claim 1, which is represented by the following Reaction Scheme 2:

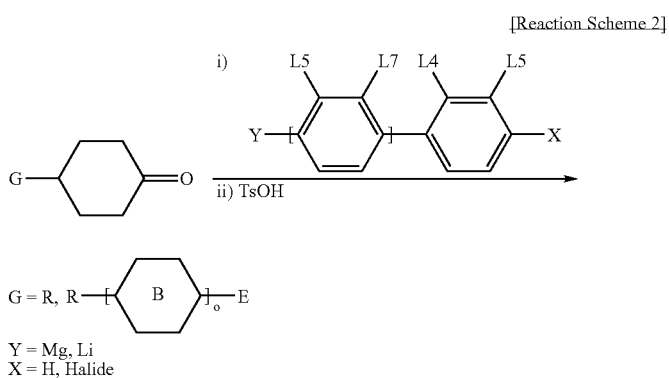

37

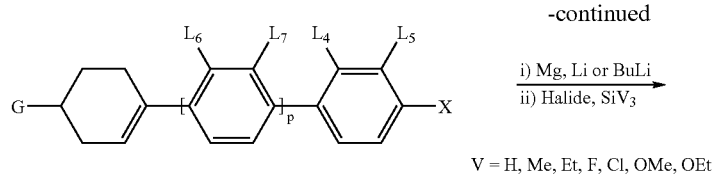

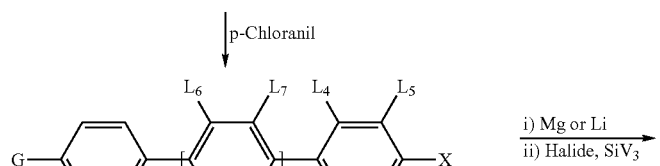

wherein V is selected from the group consisting of H, Me, Et, F, Cl, OMe and OEt; and
ring B, E, R, X, $L_4$, $L_5$, $L_6$, $L_7$, o, and p are the same as defined in claim 1.

38

-continued i) Mg, Li or BuLi
ii) Halide, $SiV_3$

V = H, Me, Et, F, Cl, OMe, OEt

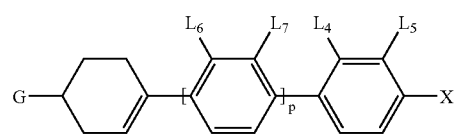

p-Chloranil i) Mg or Li
ii) Halide, $SiV_3$

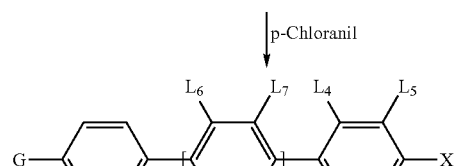

[Formula 12]

15. A method for preparing a silicon-containing compound as claimed in claim 1, which is represented by the following Reaction Scheme 3:

[Reaction Scheme 3]

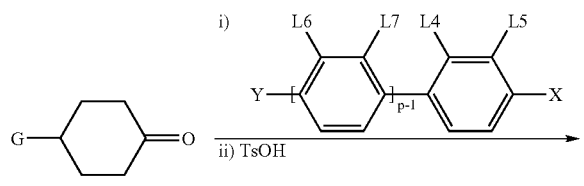

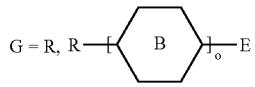

Y = Mg, Li
X = H, Halide, $SiV_3$

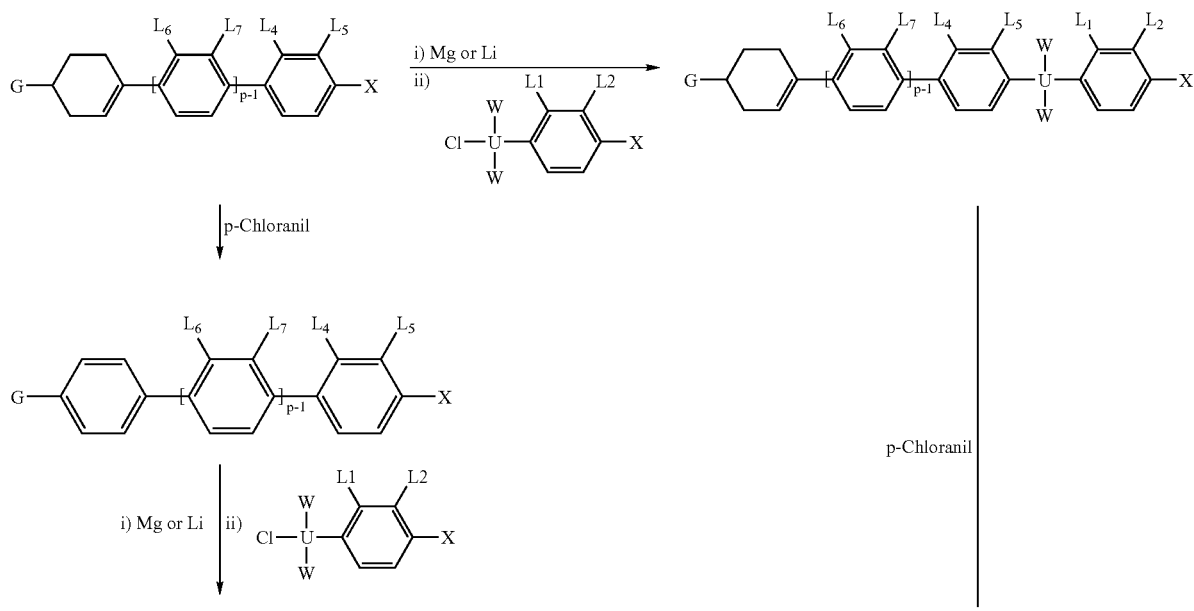

-continued

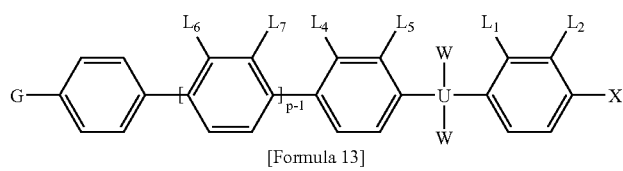

[Formula 13]

U = SiO$_{kI}$(CQ$_2$)$_{nl}$Si(CQ$_2$)$_{nl}$O$_{kii}$(CQ$_2$)$_{ni}$O$_{ki}$Si$_i$(CQ$_2$)$_{ni}$SiO$_{ki}$
W = Me, Et, F, Cl wherein U is selected from SiO$_{k1}$(CQ$_2$)$_{n1}$, Si(CQ$_2$)$_{n1}$O$_{k1}$, (CQ$_2$)$_{n1}$O$_{k1}$Si, and (CQ$_2$)$_{n1}$SiO$_{k1}$, wherein $k_1$ is 0 or 1, Q is H or F, and $n_1$ is an integer between 0 and 3, where $k_1$=0, $n_1$=0~2 and where $k_1$=1, p>0;

W is selected from Me, Et, F and Cl; and ring B, R, E, X, $L_1$, $L_2$, $L_4$, $L_5$, $L_6$, $L_7$, o, and p are the same as defined in claim 1.

16. A method for preparing a silicon-containing compound as claimed in claim 1, which is represented by the following Reaction Scheme 4:

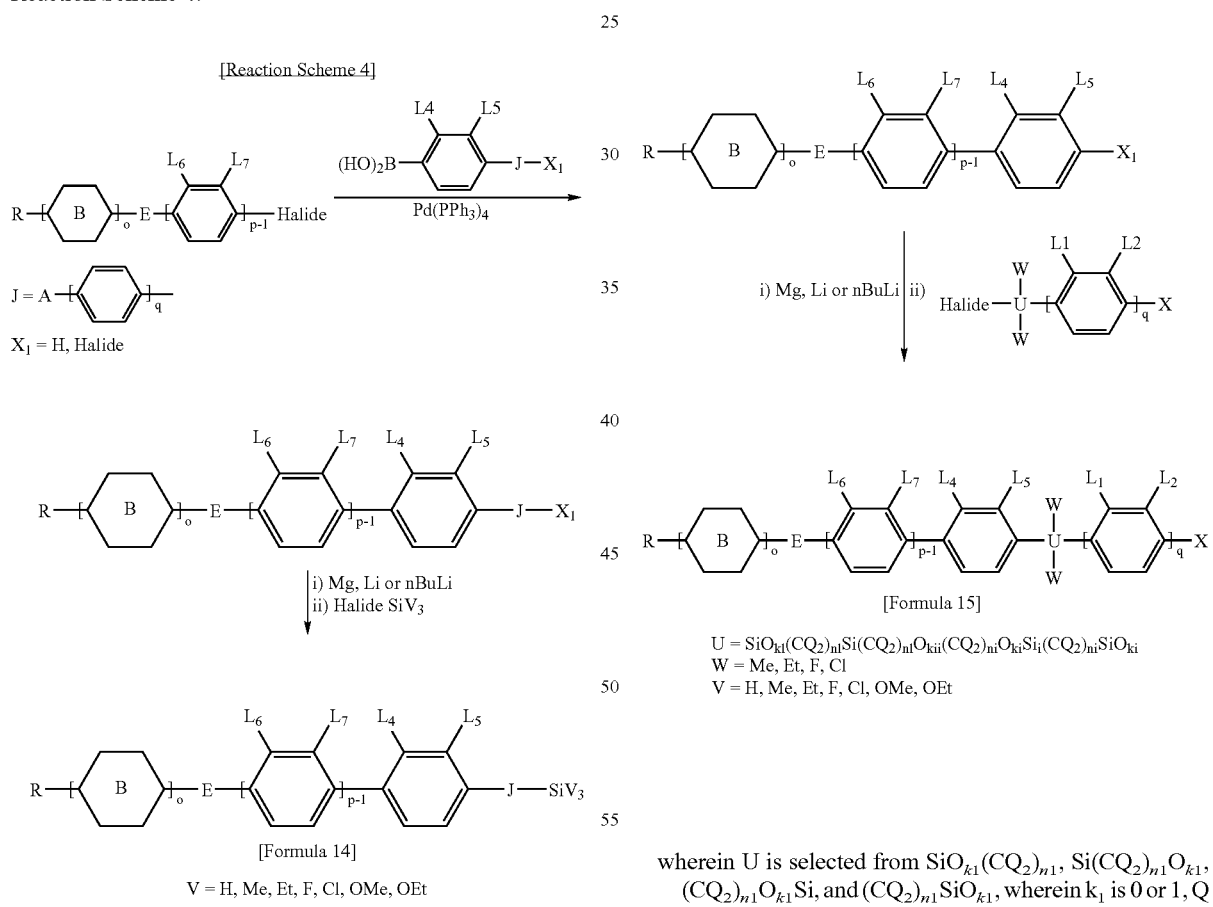

[Formula 14]

V = H, Me, Et, F, Cl, OMe, OEt wherein V is selected from the group consisting of H, Me, Et, F, Cl, OMe and OEt; and ring B, R, E, A, X, $L_4$, $L_5$, $L_6$, $L_7$, o, p and q are the same as defined in claim 1.

17. A method for preparing a silicon-containing compound as claimed in claim 1, which is represented by the following Reaction Scheme 5:

[Formula 15]

U = SiO$_{kI}$(CQ$_2$)$_{nl}$Si(CQ$_2$)$_{nl}$O$_{kii}$(CQ$_2$)$_{ni}$O$_{ki}$Si$_i$(CQ$_2$)$_{ni}$SiO$_{ki}$
W = Me, Et, F, Cl
V = H, Me, Et, F, Cl, OMe, OEt wherein U is selected from SiO$_{k1}$(CQ$_2$)$_{n1}$, Si(CQ$_2$)$_{n1}$O$_{k1}$, (CQ$_2$)$_{n1}$O$_{k1}$Si, and (CQ$_2$)$_{n1}$SiO$_{k1}$, wherein $k_1$ is 0 or 1, Q is H or F, and $n_1$ is an integer between 0 and 3, where $k_1$=0, $n_1$=0~2 and where $k_1$=1, p>0;

W is selected from Me, Et, F and Cl; and ring B, R, E, X, $L_1$, $L_2$, $L_4$, $L_5$, $L_6$, $L_7$, o, p and q are the same as defined in claim 1.

18. A method for preparing a silicon-containing compound as claimed in claim 1, which is represented by the following Reaction Scheme 6:

41
[Reaction Scheme 6]
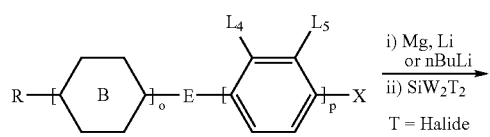
X = H, Halide
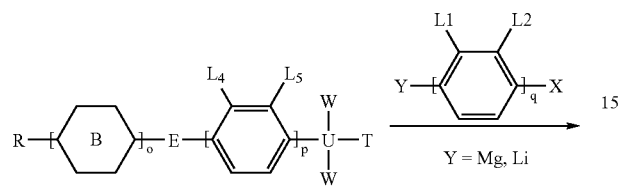
Y = Mg, Li
42
-continued
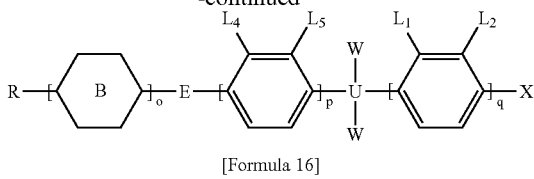
[Formula 16]
$U = SiO_{k1}(CQ_2)_{n1}Si(CQ_2)_{n1}O_{k1}$
$W = Me, Et, F, Cl$
wherein U is selected from $SiO_{k1}(CQ_2)_{n1}$ or $Si(CQ_2)_{n1}O_{k1}$, wherein $k_1$ is 0 or 1, Q is H or F, and $n_1$ is an integer between 0 and 3, where $k_1=0$, $n_1=0\sim2$ and where $k_1=1$, p>0;
W is selected from Me, Et, F and Cl; and
ring B, R, E, X, $L_1$, $L_2$, $L_4$, $L_5$, o, p and q are the same as defined in claim 1.
* * * * *